US010905394B2

(12) United States Patent
 Stigall et al.

(10) Patent No.: US 10,905,394 B2
(45) Date of Patent: Feb. 2, 2021

(54) DUAL LUMEN DIAGNOSTIC CATHETER

(71) Applicant: VOLCANO CORPORATION, San Diego, CA (US)

(72) Inventors: Jeremy Stigall, Carlsbad, CA (US); Maritess Minas, San Diego, CA (US); Princeton Saroha, Laguna Niguel, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 448 days.

(21) Appl. No.: 15/095,737

(22) Filed: Apr. 11, 2016

(65) Prior Publication Data

US 2016/0302762 A1    Oct. 20, 2016

Related U.S. Application Data

(60) Provisional application No. 62/149,928, filed on Apr. 20, 2015.

(51) Int. Cl.
*A61B 8/12* (2006.01)
*A61B 5/00* (2006.01)
(Continued)

(52) U.S. Cl.
CPC .............. *A61B 8/12* (2013.01); *A61B 5/0084* (2013.01); *A61B 8/445* (2013.01); *A61M 2025/0177* (2013.01)

(58) Field of Classification Search
CPC ......... A61B 8/12; A61B 8/445; A61B 17/221; A61B 5/0066; A61B 5/0084; A61B 2017/22068; A61B 8/0841; A61B 8/0891; A61B 2090/3784; A61B 2090/378; A61B 2090/3925; A61B 2090/3983; A61B 2090/0472; A61B 2090/3782; A61B 2018/00023; A61B 2018/00029; A61B 8/4477; A61B 8/481; A61B 8/488;
(Continued)

(56) References Cited

U.S. PATENT DOCUMENTS 4,794,931 A    1/1989  Yock
4,841,977 A    6/1989  Griffith et al.
(Continued)

FOREIGN PATENT DOCUMENTS

JP    2001245886       9/2001
WO   2014145469 A1    9/2014

OTHER PUBLICATIONS

Hausler, G. et al., "Observation of light propagation in vol. scatterers with 10-fold slow motion", Optics Letters, Jul. 1996, vol. 21, No. 14.
(Continued)

*Primary Examiner* — Theodore J Stigell
*Assistant Examiner* — Johnathan Maynard

(57) ABSTRACT

A medical device including both an intraluminal imaging apparatus and dual guidewire lumens is provided, allowing more accurate and stable catheter navigation and treatment delivery. The dual lumen catheter may also include members for increased torsional rigidity, distally located functional measurement sensors, and patterned radioopaque markers for orientation of the dual lumen exits.

19 Claims, 11 Drawing Sheets

(51) Int. Cl.
*A61B 8/00* (2006.01)
*A61M 25/01* (2006.01)

(58) Field of Classification Search
CPC ............... A61M 25/09; A61M 25/104; A61M 25/0026; A61M 2025/0183; A61M 25/0108; A61M 2025/1047; A61M 25/01; A61M 2025/0177; A61N 7/022
See application file for complete search history.

(56) References Cited

U.S. PATENT DOCUMENTS

| | | | |
|---|---|---|---|
| 4,917,097 A | 4/1990 | Proudian et al. | |
| 4,951,677 A | 8/1990 | Crowley et al. | |
| 5,000,185 A | 3/1991 | Yock | |
| 5,095,911 A | 3/1992 | Pomeranz | |
| 5,135,486 A | 8/1992 | Eberle et al. | |
| 5,167,233 A | 12/1992 | Eberle et al. | |
| 5,176,141 A | 1/1993 | Bom et al. | |
| 5,183,048 A | 2/1993 | Eberle | |
| 5,240,003 A | 8/1993 | Lancee et al. | |
| 5,243,988 A | 9/1993 | Sieben et al. | |
| 5,313,949 A | 5/1994 | Yock | |
| 5,321,501 A | 6/1994 | Swanson et al. | |
| 5,353,798 A | 10/1994 | Sieben | |
| 5,368,037 A | 11/1994 | Eberle et al. | |
| 5,373,845 A | 12/1994 | Gardineer et al. | |
| 5,373,849 A | 12/1994 | Maroney et al. | |
| 5,375,602 A | 12/1994 | Lancee et al. | |
| 5,453,575 A | 9/1995 | O'Donnell et al. | |
| 5,921,931 A | 7/1999 | O'Donnell et al. | |
| 6,134,003 A | 10/2000 | Tearney et al. | |
| 6,200,268 B1 | 3/2001 | Vince et al. | |
| 6,421,164 B2 | 7/2002 | Tearney et al. | |
| 6,659,957 B1 | 12/2003 | Vardi et al. | |
| 7,004,173 B2 * | 2/2006 | Sparks | A61B 17/3207 128/898 |
| 7,074,188 B2 | 7/2006 | Nair et al. | |
| 7,527,594 B2 | 5/2009 | Vardi et al. | |
| 7,749,168 B2 | 7/2010 | Maschke | |
| 7,783,337 B2 | 8/2010 | Feldman et al. | |
| 7,787,127 B2 | 8/2010 | Galle | |
| 7,813,609 B2 | 10/2010 | Petersen et al. | |
| 7,995,210 B2 | 8/2011 | Tearney et al. | |
| 7,999,938 B2 | 8/2011 | Wang | |
| 8,108,030 B2 | 1/2012 | Castella et al. | |
| 8,187,191 B2 | 5/2012 | Hancock et al. | |
| 8,723,361 B2 | 5/2014 | Flegel | |
| 2003/0114732 A1 * | 6/2003 | Webler | A61B 8/12 600/121 |
| 2004/0106866 A1 | 6/2004 | Ookubo et al. | |
| 2008/0119739 A1 | 5/2008 | Vardi et al. | |
| 2008/0180683 A1 | 7/2008 | Kemp | |
| 2008/0245371 A1 * | 10/2008 | Gruber | A61B 17/22 128/831 |
| 2008/0291463 A1 | 11/2008 | Milner et al. | |
| 2009/0043191 A1 | 2/2009 | Castella et al. | |
| 2010/0220334 A1 | 9/2010 | Condit et al. | |
| 2011/0152771 A1 | 6/2011 | Milner et al. | |
| 2011/0319752 A1 | 12/2011 | Steinberg et al. | |
| 2012/0230565 A1 | 9/2012 | Steinberg et al. | |
| 2013/0030295 A1 | 1/2013 | Huennekens et al. | |
| 2013/0331706 A1 | 12/2013 | Hossack et al. | |
| 2014/0180076 A1 | 6/2014 | Stigall | |
| 2015/0257779 A1 * | 9/2015 | Sinelnikov | A61B 8/12 600/439 |

OTHER PUBLICATIONS

Smith, L. et al., "Absolute displacement measurements using modulation of the spectrum of white light in a Michelson interferometer", Applied Optics, vol. 28, No. 15, Aug. 1989.

* cited by examiner

DUAL LUMEN DIAGNOSTIC CATHETER

RELATED APPLICATION

This application claims the benefit of and priority to U.S. Provisional No. 62/149,928, filed Apr. 20, 2015, which is incorporated by reference in its entirety.

FIELD OF THE INVENTION

The invention relates to medical devices and systems for use in intravascular treatment.

BACKGROUND

Intravascular catheters may be used to successfully treat a variety of medical problems including chronic total occlusions, thrombosis, hypertension, and atherosclerosis. These catheters have the potential to save lives when used effectively and efficiently.

Intravascular treatment via catheter, especially in tortuous vasculature, requires a high degree of precision. Current devices can prove inaccurate, leading to ineffective treatment by missing the treatment target or causing complications such as trauma to, or perforation of, the vessel wall. Accordingly, safe treatment with catheters can require the use, and exchange, of multiple separate devices for tasks such as intravascular imaging, steering, and treatment. Each of these individual devices must be advanced through the vasculature, removed, and replaced with the next device. Some procedures may require multiple exchanges such as insertion and removal of an imaging device for pre-treatment navigation and post-treatment verification. Patient risk is increased as each device exchange introduces additional opportunities for vascular trauma and other complications. Furthermore, many external imaging techniques require exposure to x-rays and other potentially harmful radiation and prolonging procedures likewise prolongs the exposure.

SUMMARY

The disclosed invention generally relates to medical devices, systems, and methods for providing intravascular treatment with dual guidewire lumens with imaging capabilities near the distal exit ports of at least one lumen. By providing intravascular imaging capability directly at a lumen exit port, the need to exchange imaging and treatment catheters is avoided. Additionally, the two lumens allow easy guidewire exchange as one guidewire and lumen may be used for support while another guidewire is advanced in the other lumen. The two lumens also improve steering capability by allowing the use of shaped wires for side branch access and navigating bifurcations. Additionally, substantially parallel orientation of the two lumens at the distal portion of the catheter provides improved centering of the catheter body during use. The elements of the inventive catheters can provide real-time imaging of the treatment site during treatment and may reduce the need for exchanges of separate devices, minimizing the associated risk of vascular trauma and reducing procedure time.

By setting the distal exits of both lumens near the location of an imaging apparatus, the catheter allows a user to make navigation and therapy delivery decisions with reference to images obtained from the delivery location. Locating one or more of the exit ports of a dual lumen catheter near an imaging apparatus can allow accurate delivery of an appropriate treatment to a target area with minimal adjustments. A distally located imaging apparatus may also be used to monitor and verify the effectiveness of treatment during and after delivery.

Guidewire lumens may be of any suitable type such as over-the-wire (OTW), which allow for easy exchange of guidewires, or rapid exchange (RX), which can be more quickly threaded and require shorter guidewires. In certain embodiments, catheters of the invention may include one OTW guidewire lumen and one RX guidewire lumen, taking advantage of both types. Guidewire lumens may have exit ports on the distal portion of the catheter and within a short distance of the imaging apparatus. In various embodiments, one or both of the lumens may pass through the imaging apparatus. Lumen exit ports may be proximal or distal to the imaging apparatus and may be adjacent one another or offset. Exit ports may be flat or may be skive cut to form an angle with the distal portion of the catheter body, allowing for easier passage of the catheter through the vasculature.

An imaging apparatus may include an ultrasound transducer as part of an intravascular ultrasound (IVUS) assembly. In some embodiments, the imaging apparatus may be an optical coherence tomography (OCT) imaging apparatus. Optionally, the distal portion of the catheter may include a functional measurement sensor configured to sense parameters such as pressure, velocity, or Doppler velocity. The distal portion may include a transducer support configured to support a variety of imaging assemblies. In certain embodiments, imaging assemblies may be interchangeably affixed to the transducer support.

To aid in visualization and orientation of the distal portion of the body and the exit ports within vasculature, the distal portion of the catheter body may include a pattern of radioopaque or other markers that may be externally monitored by, for example, x-ray. Catheter bodies may include a variety of features to efficiently transfer axial torque applied at the proximal end of the catheter to the distal end of the catheter, easing manipulation of the distal end during navigation or treatment deliver. Catheters of the invention may be compatible with automated body lumen measurement software such as VH® IVUS from Volcano Corporation (San Diego, Calif.), image highlighting software for blood, plague, and foreign body differentiation such as Chroma-Flo® from Volcano Corporation (San Diego, Calif.), and software for correlating a single view from IVUS and angiogram images such as SyncVision™ from Volcano Corporation (San Diego, Calif.).

Catheters of the invention may be used for crossing a chronic total occlusion, tissue ablation, thrombolysis, drug dispersion, aspiration, echogenic injection, to navigate through bifurcations or for side branch access. The combination of two guidewire lumens, external orientation tracking, efficient axial torque transfer, and localized intravascular imaging at the lumen exit ports provides delivery of catheter based treatments that are quicker, safer, and more accurate and effective than provided by current catheters. Catheters of the invention may include centering mechanisms including inflatable balloons, or collapsible members (e.g., a sheathable nitinol basket) of various shapes and sizes disposed near the distal end of the catheter and the first and/or second exit ports. Centering mechanisms can be configured to interact with a lumen wall in order to center the first and/or second exit ports within a cross-section of the vessel, artery, or other lumen. Catheters of the invention may include perfusion holes In certain aspects, the invention relates to an intravascular treatment catheter having an elongated body with a distal portion and a proximal portion. The catheter has an imaging apparatus at the distal portion of the body configured to image a location within vasculature. The catheter body includes a first guidewire lumen with a first exit port disposed at the distal portion of the body and a second guidewire lumen substantially parallel to the first at least at the distal portion of the body with a second exit port also disposed at the distal portion of the body.

The imaging apparatus can include an ultrasound transducer which may be an intravascular ultrasound (IVUS) imaging apparatus with a micromachined ultrasonic transducer. In some embodiments, the imaging apparatus may include an optical coherence tomography (OCT) imaging apparatus. The catheter may also include a functional measurement sensor such as a pressure sensor, a velocity sensor, a Doppler velocity sensor, or an optical sensor, at the distal portion of the body.

In various embodiments, the first guidewire lumen of the catheter may be an over-the-wire guidewire lumen and the second guidewire lumen may be a rapid exchange guidewire lumen. The first exit port and the second exit port may be offset from each other and either or both may be located within 5 cm of the imaging apparatus. In certain embodiments, at least one of the first and second exit ports forms an obtuse angle with a line tangential to the distal portion of the elongated body.

The imaging apparatus may be located distal to the first exit port. In some configurations, the catheter may include a shaft, a braided material, or a coiled material or may be otherwise configured to transmit axial torque applied to the proximal portion of the body to the distal portion of the body.

In certain embodiments, the imaging apparatus is disposed around the second guidewire lumen. The distal portion of the catheter body may include a pattern configured to show an orientation of the distal portion of the body under x-ray imaging. The catheter may include a third lumen and a microcable therein with the microcable extending from the imaging apparatus to the proximal portion of the catheter and in electronic communication with the imaging apparatus.

In certain aspects, the invention provides methods of delivering intravascular treatment. The methods include advancing a first guidewire substantially to a portion of a vessel to be treated, advancing an intravascular treatment catheter over the first guidewire, imaging the portion of the vessel to be treated, and delivering treatment. The intravascular treatment catheter includes an elongated body having a distal portion and a proximal portion, and an imaging apparatus at the distal portion. The imaging apparatus is configured to image the portion of the vessel to be treated. The intravascular treatment catheter includes a first guidewire lumen having a first exit port and a second guidewire lumen substantially parallel to the first guidewire lumen at least at the distal portion of the body and having a second exit port. Both the first and second exit ports may be at the distal portion of the catheter body.

Methods of the invention may include steering the intravascular treatment catheter through one selected branch of a bifurcation in the vasculature. Steering the catheter may be accomplished by advancing the first guidewire to the bifurcation, advancing the catheter over the first guidewire to the bifurcation, imaging the bifurcation and then selecting a shaped guidewire configured to enter the desired branch of the bifurcation. The shaped guidewire is advanced through the second guidewire lumen and into the desired branch of the bifurcation, after which the catheter may be advanced over the shaped guidewire into the desired branch.

In some embodiments, methods can include treating a chronic total occlusion by advancing the catheter along the first guidewire to the chronic total occlusion. Preferably, the catheter includes a functional measurement sensor configured to sense pressure and located at the distal portion of the body. The functional measurement sensor may be used to verify position of the distal portion of the body at the chronic total occlusion by sensing a change in pressure. Methods of the invention may include using the first guidewire for support while crossing the chronic total occlusion with a second guidewire advanced through the second guidewire lumen; and delivering a therapy to the chronic total occlusion.

DETAILED DESCRIPTION

The invention generally relates to dual lumen intravascular treatment catheters with an imaging apparatus near the distal exits of both lumens, allowing a user to make steering and treatment decisions based on direct imaging from the lumen exits and accurately deliver the appropriate treatment to the target area with very minimal adjustments. The presence of two lumens allows for increased support, improved catheter centering, and improved steering through the use and easy exchange of various shaped guidewires. Additional features of the catheter may include various means of increased torsional rigidity for better axial torque transmission to the distal end of the catheter. Catheters of the invention may also include a pattern of radioopaque markers or other means for external determination of catheter orientation at the distal portion. In certain instances the distal portion of the catheter may include additional functional measurement sensors to aid in navigation and the accurate delivery of treatment.

Catheter Body

Figure 1:
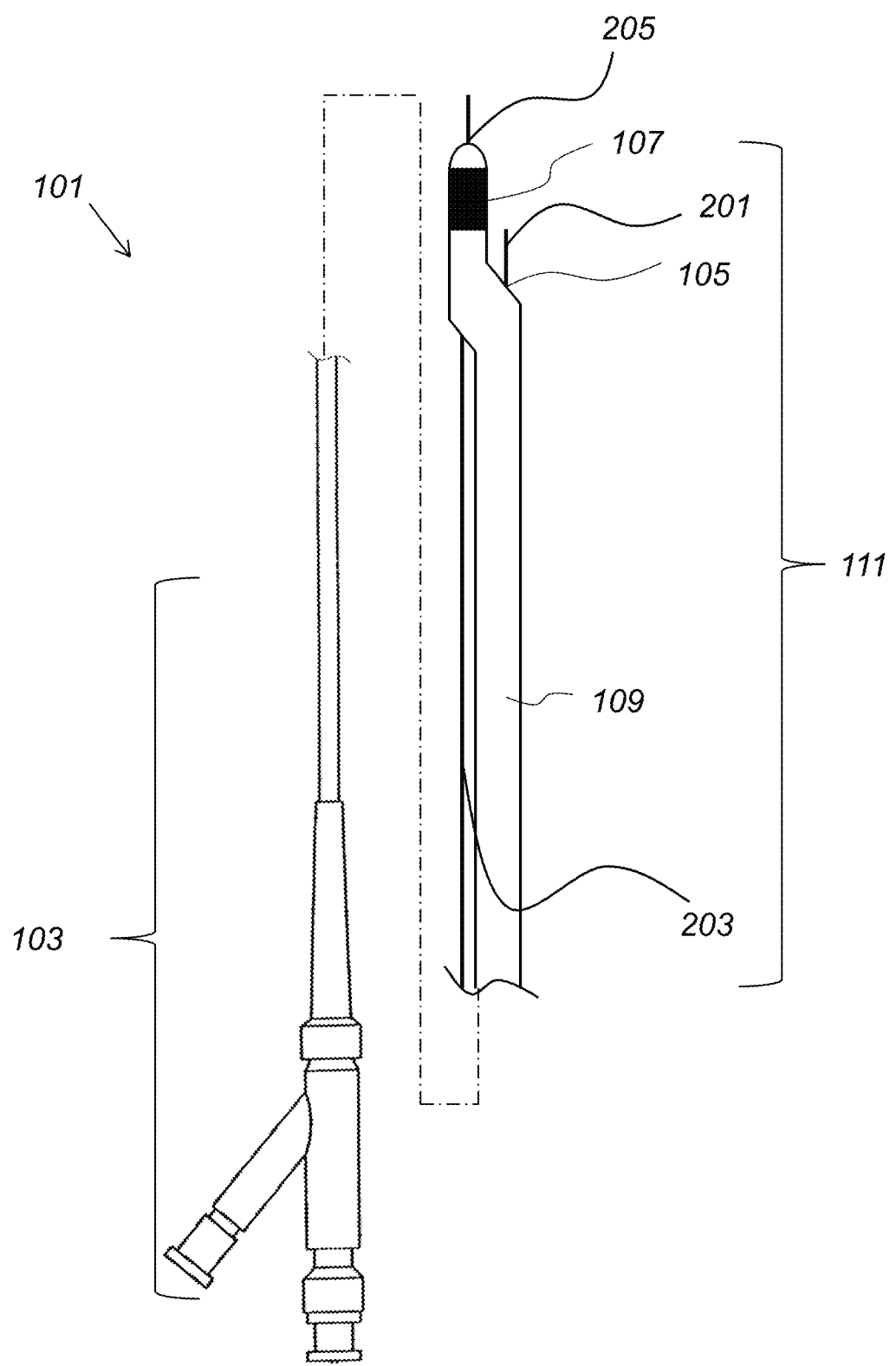
FIG. 1 shows a dual lumen catheter assembly.

FIG. 1 shows a catheter 101 with an elongated body 109 having an OTW guidewire 201 and a RX guidewire 203 disposed within the elongated body 109 in first and second guidewire lumen (not shown) respectively and exiting through a first exit port 105 and a second exit port 205 respectively. Catheter 101 generally includes a proximal portion 103 extending to a distal portion 111. An imaging apparatus 107, such as an ultrasound transducer, may be located at the distal portion 111.

In the intravascular catheter is configured for intraluminal introduction to a target body lumen. The dimensions and other physical characteristics of the catheter bodies will vary significantly depending on the body lumen that is to be accessed. Catheters of the invention may include two or more lumens. Lumens may be a variety of types including "over-the-wire" (OTW) where a guidewire channel extends fully through the catheter body or for "rapid exchange" (RX) where the guidewire channel extends only through a distal portion of the catheter body. In an exemplary embodiment, as shown in FIG. 1, a catheter of the invention may include at least one RX and at least one OTW lumen to exploit the unique advantages of each type of guidewire lumen.

The catheter may include additional lumens to house microcables in electronic communication with the imaging apparatus, support or torsion members, drive shafts or cables, or other purposes.

The dual lumens may be substantially parallel over the course of the catheter body. In certain embodiments, the lumens may be substantially parallel only at the distal portion of the catheter and/or at their respective exit ports.

Catheter bodies intended for intravascular introduction will typically have a length in the range from 50 cm to 200 cm and an outer diameter in the range from 1 French to 12 French (0.33 mm: 1 French), usually from 3 French to 9 French. Catheter bodies will typically be composed of an organic polymer that is fabricated by conventional extrusion techniques. Suitable polymers include polyvinylchloride, polyurethanes, polyesters, polytetrafluoroethylenes (PTFE), silicone rubbers, natural rubbers, and the like. Optionally, the catheter body may be reinforced with braid, helical wires, coils, axial filaments, or the like, in order to increase qualities such as rotational strength, column strength, toughness, or pushability. Suitable catheter bodies may be formed by extrusion, with one or more channels being provided when desired. The catheter diameter can be modified by heat expansion and shrinkage using conventional techniques. The resulting catheters will thus be suitable for introduction to the vascular system, often the coronary arteries, by conventional techniques.

Figure 11:
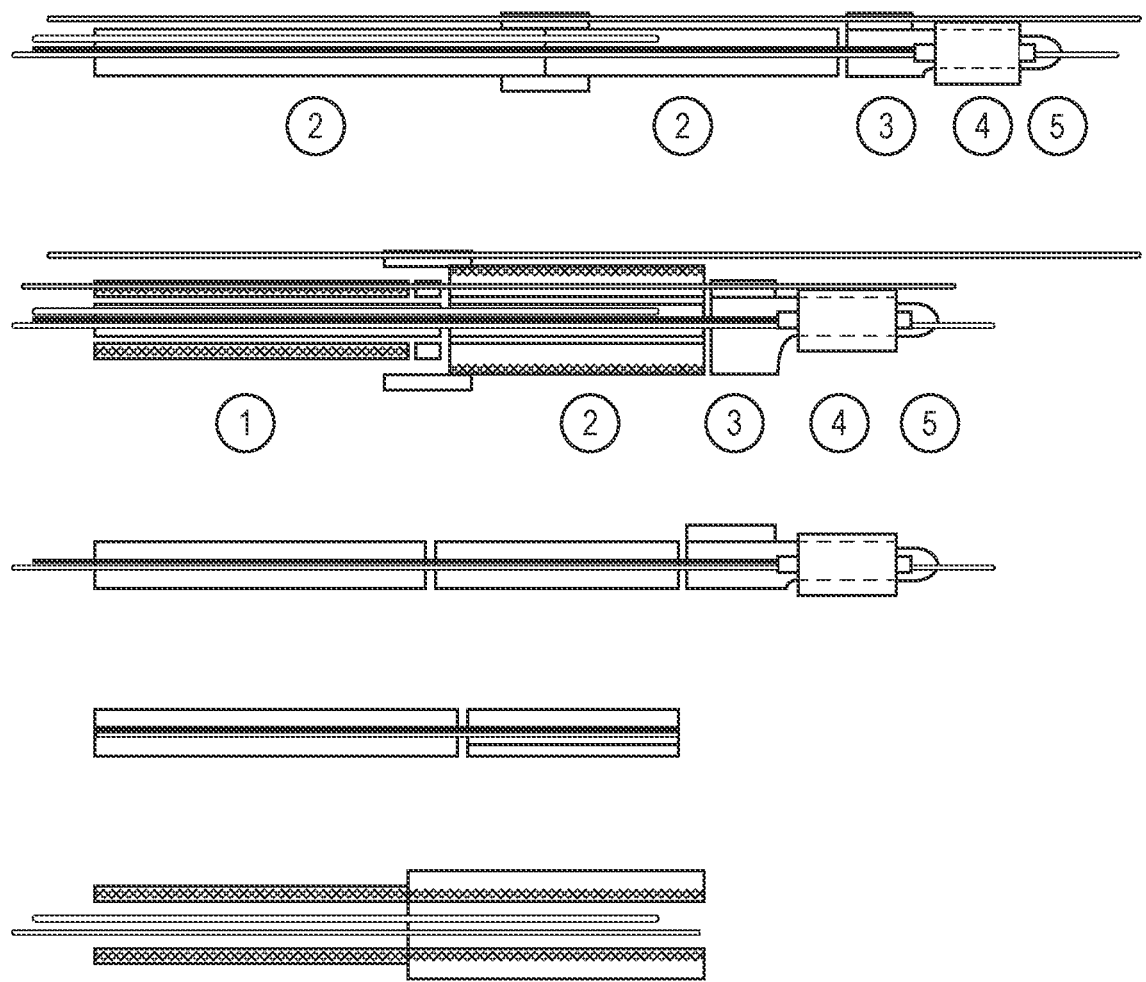
FIG. 11 shows five examples of catheter body configurations for axial torque transmission.

As noted, in certain aspects, the catheter body may be reinforced for torsional rigidity to increase axial torque transmission from the proximal to distal portion of the body. Torsional rigidity may be augmented through a variety of torsion members including wires, spines, shafts, braided or coiled materials, or a combination thereof. These members may be disposed around, on, or within some portion of the catheter body. Various members for increasing torsional rigidity are shown in FIG. 11. An axial torque transmitting shaft may be an extruded single lumen, an extruded dual lumen, or an extruded single lumen with two shafts running through it. These lumens may be free floating or fixed between the proximal and distal ends of the catheter body but, in most embodiments, should be fixed to one or more of the guidewire lumens at the distal portion of the body. Fixation may be through heat fusion, adhesive, or other means known in the art. In certain embodiments, the axial torque transferring mechanism may include a separate lumen with a shaft run therethrough as shown in example #1 of FIG. 11. The separate lumen, additional to the dual guidewire lumens, may run the length of the catheter body and may be fixed to the catheter body at least at the distal portion near the first and second exit ports and the imaging apparatus. The separate lumen should form a tight fit over the shaft to resist axial movement of the shaft relative to the separate lumen. The shaft can act as a spine to transfer axial torque and may be constructed of a variety of materials including metal, fiber, composite, and plastics or other polymers.

In certain aspects, the catheter may include a shaft made up a of braided or coiled material, as shown in example #2 of FIG. 11, where the braided or coiled material is terminated at the distal and proximal ends in circumferential bands. The shaft may be terminated by coupling the cut braids at both proximal and distal ends with small bands or reducing the pitch of a coil at both ends until the coils are substantially touching. The shaft may be coupled to one or both of the guidewire lumens or otherwise joined to the catheter body at least at the distal portion. A torsion shaft may be incorporated in the construction of the catheter. In certain aspects, the inner diameter of the catheter body may be lined with a polymeric liner and the entire assembly may be reflowed to integrate the shaft into the catheter body. In some embodiments, the small bands coupling the cut braids at the distal and proximal ends of the shaft may be constructed of a polymer and can provide a surface which is easier to bond to the catheter body during manufacturing.

In some instances, catheters may include a hypotube inserted into a guidewire or microcable lumen as shown in example #3 in FIG. 11 the hypotube may, like the separate lumen in example #1, tightly fit around a shaft and be fixed to the catheter body, at least at the distal portion, to provide a spine like support. In certain aspects, and as shown in example #4 of FIG. 11, a third lumen may be constructed into the distal portion of the catheter while the proximal portion comprises two lumens. The third lumen may provide additional torsional rigidity at the distal portion of the catheter and may tightly contain a shaft as described in example #1. In some embodiments, and as shown in example #5 in FIG. 11, a braided shaft constructed from, for example, a polymer, may be inserted into a compatible polymer jacket and fused with heat or by chemical process to the RX lumen or the distal portion of the OTW lumen.

The distal portion of the body, an imaging apparatus support, and/or a tracking tip include a pattern of markings positioned to show orientation of the distal portion of the body, an imaging apparatus support, and/or a tracking tip and to aid in navigation of the catheter and/or treatment delivery. Markings may be radioopaque so that they are observable from outside of the body using x-rays. Markers may be embedded inside the body of the device, and can be dimensioned to be compatible with various monitoring software such as software for correlating a single view from IVUS and angiogram images (e.g., SyncVision™, Volcano Corporation, San Diego, Calif.).

To aid in visualization and orientation of the distal portion of the body and the exit ports within vasculature, the distal portion of the body may include a pattern of radioopaque or other markers which may be externally monitored via, for example, x-ray.

In certain embodiments, catheters of the invention may include one or more centering mechanisms disposed on the catheter body, catheter tip, or the imaging apparatus support. Centering mechanisms may be disposed at any suitable location along the length of the catheter body. In preferred embodiments, centering mechanisms are disposed near the distal end of the catheter and/or the first and/or second exit ports so that the first and/or second exit ports may be centered within a vessel by the centering mechanism. Centering mechanisms may include, for example, inflatable balloons, or collapsible structures such as a sheathable nitinol basket or other structure comprising a shape memory material. Centering mechanisms may have an unexpanded state in which they remain close to the catheter body and an expanded state wherein the centering mechanism expands radially from the surface of the catheter body in order to interact with a lumen wall to center the first and/or second exit ports within a cross-section of a vessel, artery, or other body lumen. A balloon centering mechanism may transition between an unexpanded and expanded state through application of a fluid or gas to inflate the one or more balloons. The catheter body may include an air or fluid line connecting the balloon centering mechanism to a an air or fluid source. A pump may be used to force air or fluid into the centering balloon in order to expand it. Balloon centering mechanisms may be of any suitable shape or size.

Figure 13:
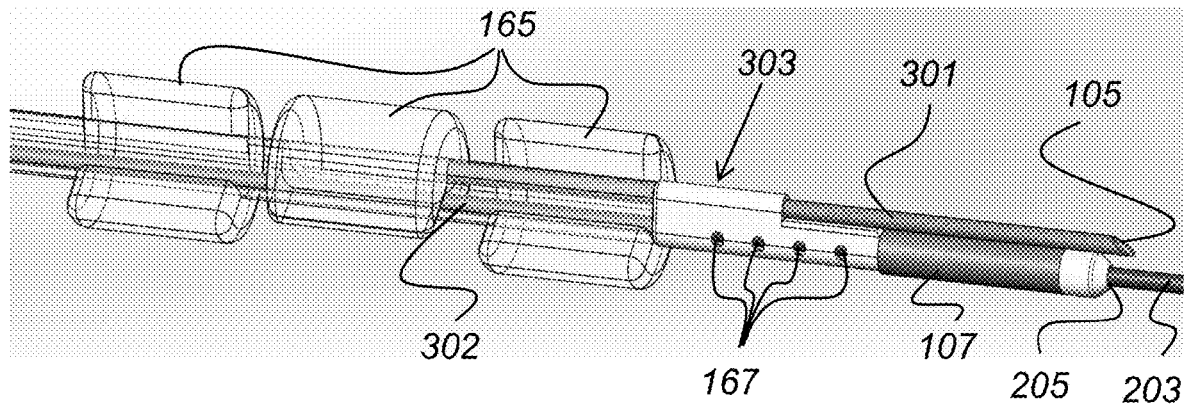
FIG. 13 shows a dual lumen imaging apparatus with perfusion holes and a multiple balloon centering mechanism.
Figure 14:
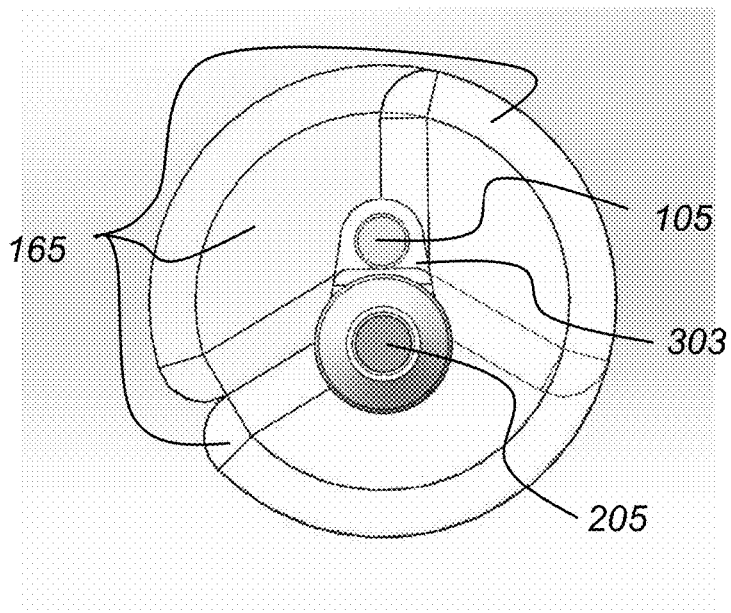
FIG. 14 shows a head-on view of the distal end of a dual lumen imaging apparatus with a multiple balloon centering mechanism.
Figure 15:
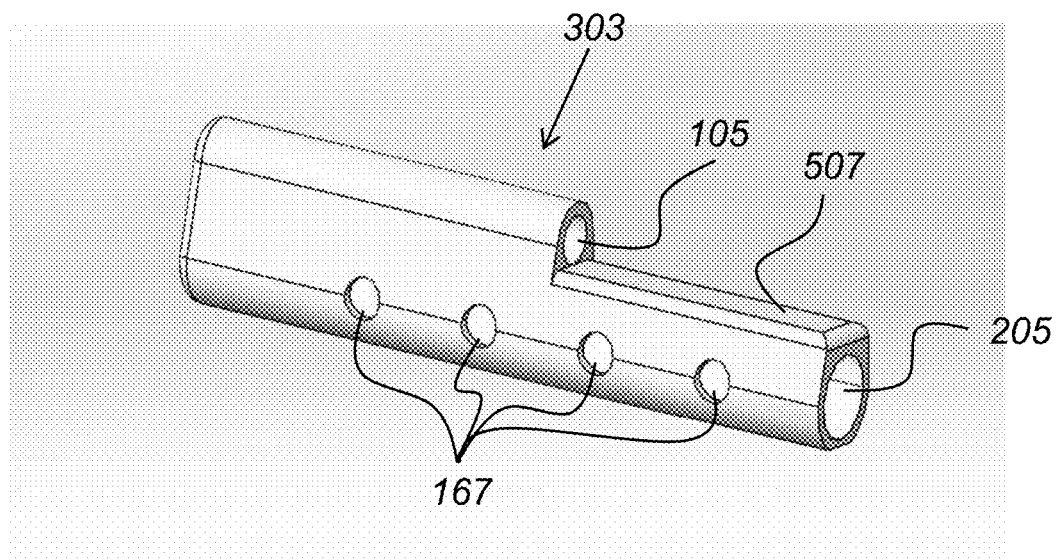
FIG. 15 shows a dual lumen imaging apparatus support with perfusion holes.

FIG. 13 shows an exemplary catheter configuration wherein three separate centering mechanisms 165 are spaced apart along the catheter body near an imaging apparatus support 303. The imaging apparatus support 303 comprises an imaging apparatus 107, a plurality of perfusion holes 167, a first guidewire lumen 301 having a first exit port 105 and a second guidewire lumen 302 having a second exit port 205 and containing a second guidewire 203. The centering mechanisms 165 are balloons which, when inflated, comprise a C-shaped cross section and surround a portion of the circumference of the catheter body. The three centering mechanisms 165 are positioned relative to each other so that the gaps in the C-shaped cross sections are offset from each other along the circumference of the catheter cross section as shown in FIG. 14. By offsetting the gaps, the balloon catheters provide a centering force to the catheter against a lumen wall around the entire circumference of the catheter surface while maintaining an open flow path for blood or other fluids within the body lumen. This may allow the centering mechanism to be used during treatment without disrupting blood flow within the lumen being treated, thereby avoiding problems caused by lack of blood flow to tissues and enabling sensors on the catheter to accurately track pressure or flow within the lumen in order, for instance, to determine effectiveness of a treatment such as removal of an occlusion. Balloon centering mechanisms may be placed in offset of one another along the device anywhere proximal first exit port 105 on the distal end of the catheter. Balloon centering mechanisms may be segmented circles with open sections to allow blood flow through. A helical open section orientation between multiple balloons may optimize centering efficiency, and blood flow rate. A profile view of the catheter shows that these balloons should center the device from 360° around the circumference of the catheter body. Multiple centering mechanisms 165 as shown in FIGS. 13 and 14, may allow for individual inflation or expansion so that only those centering mechanisms that are necessary need be deployed. In certain embodiments, multiple centering mechanisms 165 may be have a variety of sizes and shapes so that one or more centering mechanisms 165 may be selectively expanded based on the size and shape of the body lumen in which they are being deployed.

Figure 16:
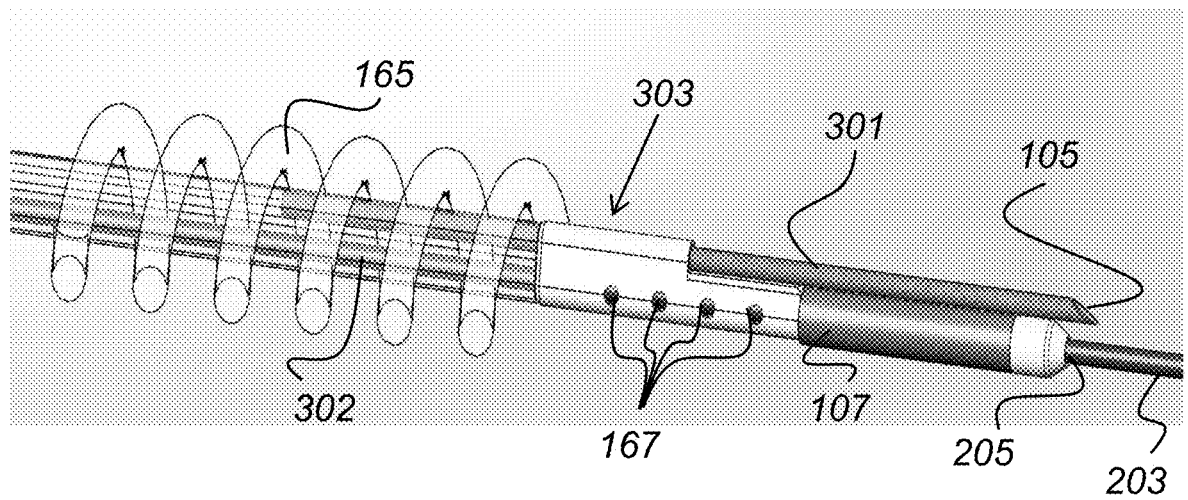
FIG. 16 shows a dual lumen imaging apparatus with perfusion holes and a spiral-shaped balloon centering mechanism.

FIG. 16 shows a spiral-shaped balloon centering mechanism 165 which spirals around the circumference of the catheter body near the distal end of the catheter and the imaging apparatus support 303, proximal to the imaging apparatus 107 and the first 105 and second 205 exit ports. The imaging apparatus support 303 comprises an imaging apparatus 107, a plurality of perfusion holes 167, a first guidewire lumen 301 having a first exit port 105 and a second guidewire lumen 302 having a second exit port 205 and containing a second guidewire 203. The spiral-shaped centering mechanism 165 may enable greater flexibility of the catheter body than other designs, particularly when expanded. The spiral-shaped centering mechanism 165 provides centering force around the entire circumference of the outer catheter surface while maintaining an open flow path for blood or other fluids within the lumen.

Figure 17:
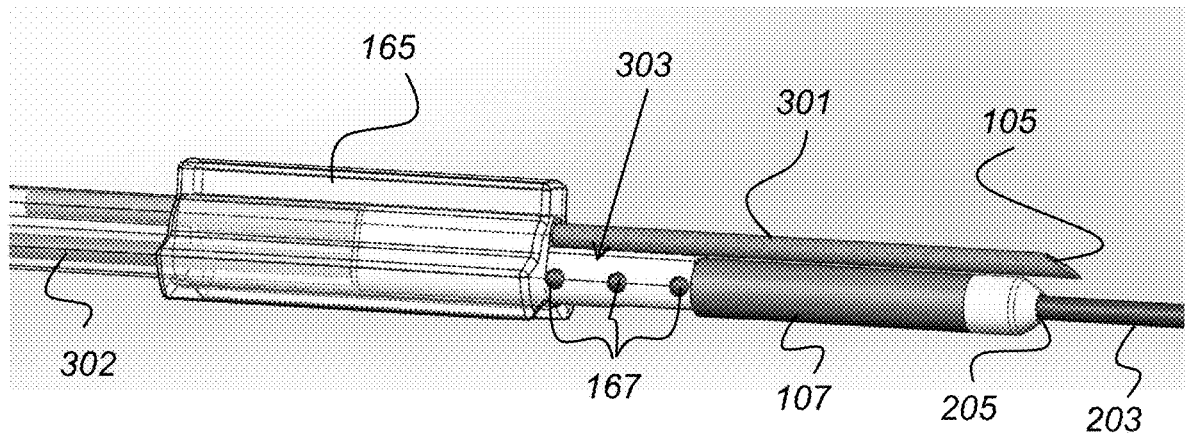
FIG. 17 shows a dual lumen imaging apparatus with perfusion holes and a balloon centering mechanism having a cross-sectional shape of a segmented circle with multiple open sections.
Figure 18:
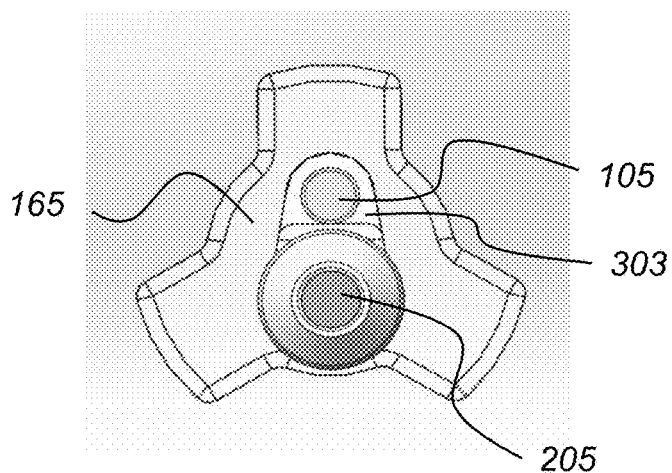
FIG. 18 shows a head-on view of the distal end of a dual lumen imaging apparatus with a balloon centering mechanism having a cross-sectional shape of a segmented circle with multiple open sections.

FIGS. 17 and 18 show a centering mechanism 165 comprising a balloon placed immediately proximal of the imaging apparatus support 303, the imaging apparatus 107, and the first 105 and second 205 exit ports, allowing the first (not shown) or second 203 guidewire to exit in the center of the centering mechanism 165 while preventing any damage thereto. The imaging apparatus support 303 comprises an imaging apparatus 107, a plurality of perfusion holes 167, a first guidewire lumen 301 having a first exit port 105 and a second guidewire lumen 302 having a second exit port 205 and containing a second guidewire 203. Disposing the centering mechanism 165 near the first 105 or second 205 exit port may provide more effective centering of those ports than where the centering mechanism 165 is disposed at a distance. The centering mechanism 165 shown in FIGS. 17 and 18 is a single segmented circle balloon with multiple open sections. A single segmented circle may provide circumferential centering force for the catheter against the wall of the body lumen while maintaining a blood or fluid flow path through the multiple open sections.

In various embodiments, a centering mechanism may comprise a collapsible structure such as a nitinol basket wherein a sheath maintains the mechanism in a collapsed, unexpanded state close to the catheter body and, when the sheath is removed, the mechanism expands. A sheath may be coupled to a release mechanism so that it may be manipulated from the proximal end of the catheter. In certain aspects, the sheath may be configured to be removed and replaced so that the centering mechanism may be collapsed after treatment for ease of removal from the vasculature.

In certain embodiments, a catheter with a centering mechanism may be advanced through the vasculature to a desired treatment location at which point the centering mechanism may be expanded or deployed in order to center the catheter and/or one or more exit ports thereof within the vasculature. Treatment may then be applied and the centering mechanism may be collapsed before removal of the catheter from the vasculature.

Dual Lumen Transducer Support

In certain embodiments, the distal portion of a catheter body may comprise an imaging apparatus, or transducer, support configured to house the imaging apparatus and the first and/or second exit ports. The transducer support may include an integrated tip or may be coupleable to a variety of interchangeable tips which may be selected based on the application. The transducer support may include features such as glue port holes to aid in catheter construction and/or functional measurement sensors for parameters such as pressure, flow, and velocity and may comprise, for example, optical sensors, microfabricated microelectromechanical (MEMS) pressure sensors, or ultrasound transducers, including Doppler velocity sensors, to measure the parameters.

Figure 2:
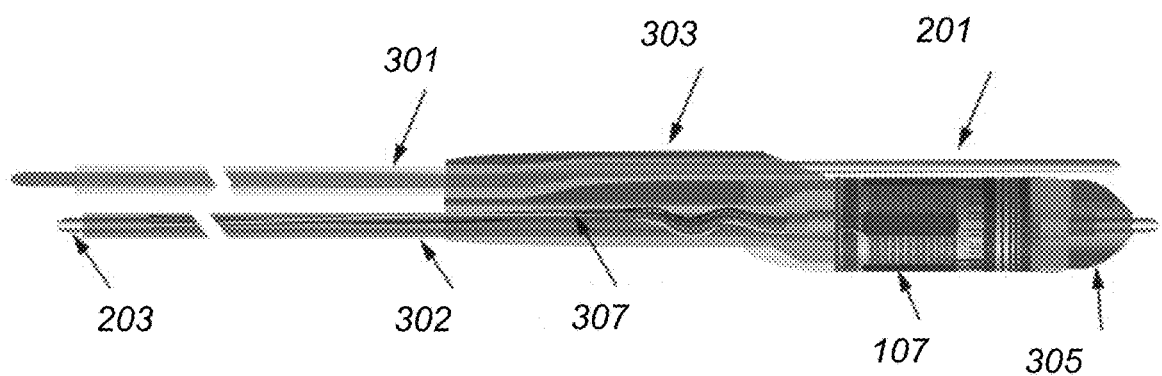
FIG. 2 shows a distal portion of a dual lumen catheter assembly.

FIG. 2 shows an imaging apparatus support 303 with a first guidewire lumen 301 of the OTW type containing a first guidewire 201. The imaging apparatus support 303 includes an imaging apparatus 107 with a separate, short, single lumen tip 305 and a RX-type second guidewire lumen 302 disposed through the imaging apparatus 107 and the tip 305 and exiting therethrough. A second guidewire 203 is disposed within the second guidewire lumen 302 along with a microcable 307 connected to the imaging apparatus 107

In some aspects, the transducer support may be rigid in order to maintain a relative orientation between the first and second exit ports, the imaging apparatus, and in some instances a functional measurement sensor. In most embodiments the imaging apparatus support may have a diameter that generally matches the proximal portion of the catheter body, however, in other embodiments, the distal portion may be larger or smaller than the proximal portion of the catheter. The imaging apparatus support can be formed from materials that are rigid or which have very low flexibilities, such as metals, hard plastics, composite materials, NiTi, steel with a coating such as titanium nitride, tantalum, ME-92 (antibacterial coating material), or diamonds. Most usually, the distal end of the catheter body will be formed from stainless steel or platinum/iridium.

Figure 7:
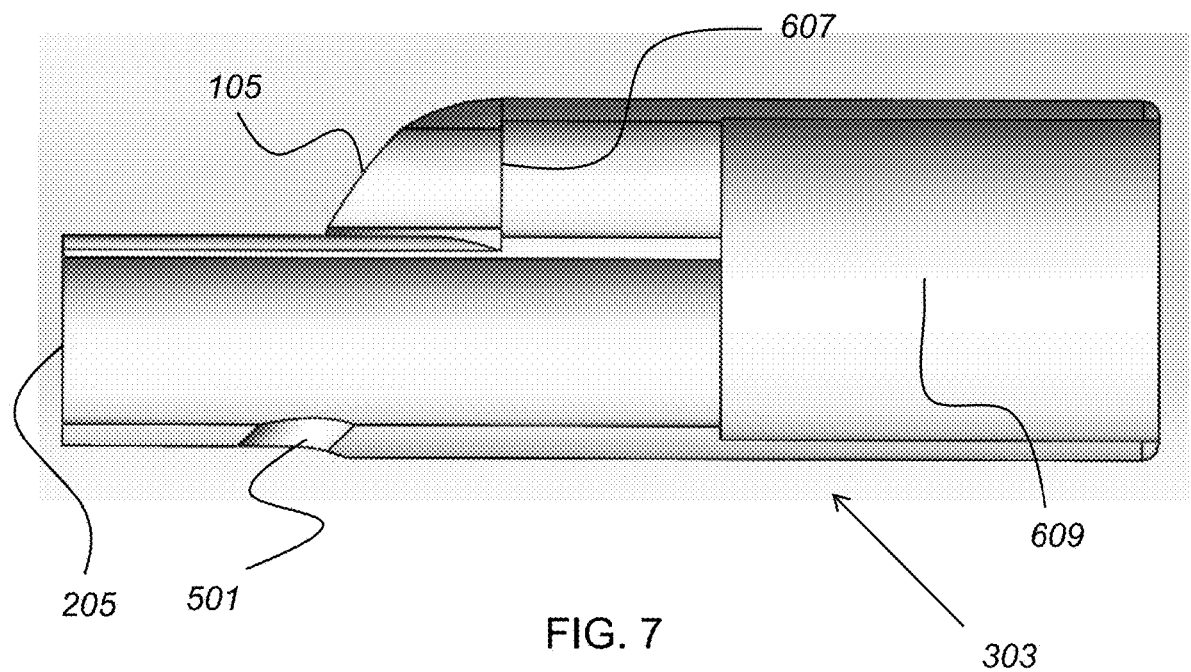
FIG. 7 shows a dual lumen imaging apparatus support with offset exit ports, an angle cut exit port and a glue port hole.

Imaging apparatus supports and/or tracking tips may be constructed with one or more lumens and may be extruded from a raw material or additive manufactured using, for instance, 3D printing techniques. Imaging apparatus supports and/or tracking tips may also be made through molding casting or other suitable construction techniques known in the art and suited to the material from which the component is constructed. FIG. 7 shows a cutaway view of an imaging apparatus support 303 including a first exit port 105 offset from a second exit port 205, and also including a glue port 501 to aid in catheter construction. Imaging apparatus supports and/or tracking tips may include a step 607 in an inner lumen. The inner lumen may have a greater diameter than the first or second guidewire lumen proximal to the step 607 and may have a lesser diameter than the first or second guidewire lumen distal to the step 607. In certain embodiments, the inner lumen of the imaging apparatus support or a tracking tip may taper, narrowing toward their distal ends or toward steps 607. The inner lumen and/or step 607 of an imaging apparatus support or tracking tip may help during construction of the catheter by centering the guidewire lumen as it is inserted into the imaging apparatus support or tracking tip and providing a stop to indicate full insertion. The imaging apparatus support or tracking tip may also include one or more glue ports 501 through which an adhesive may be introduced to secure a guidewire lumen to the imaging apparatus support or tracking tip after the guidewire lumen has been inserted therein. An imaging apparatus support or tracking tip may include a single proximal inner lumen 609 which separates into multiple distal inner lumens. The separate distal inner lumens may provide a localized joint just proximal to the imaging apparatus and/or exit ports that forces both guidewire lumens to realign parallel to one another. Parallel lumens near the imaging apparatus and/or the exit ports may increase the centering strength of the RX guide wire when delivering treatment through the OTW lumen or vice versa.

In certain instances, the imaging apparatus support may be integrally formed with the catheter body and/or a single or dual lumen tip. In embodiments with a dual lumen tip, the exit port for one of the lumens can be disposed on the imaging apparatus support or the distal portion of the catheter body. In preferred embodiments, the first and second exit ports are disposed near the imaging apparatus and, in embodiments including an imaging apparatus support, the support. The first exit port, the second exit port, or both, may be located within 1 cm, 2 cm, 3 cm, 4 cm, 5 cm, 6 cm, 7 cm, 8 cm, 9 cm, or 10 cm of the imaging apparatus or imaging apparatus support. The first exit port may be disposed on the catheter distal to or proximal to the imaging apparatus support or the imaging apparatus. The second exit port may be disposed on the catheter distal to or proximal to the imaging apparatus support or the imaging apparatus. The two exit ports may or may not be disposed on the same side of the imaging apparatus.

Figure 5:
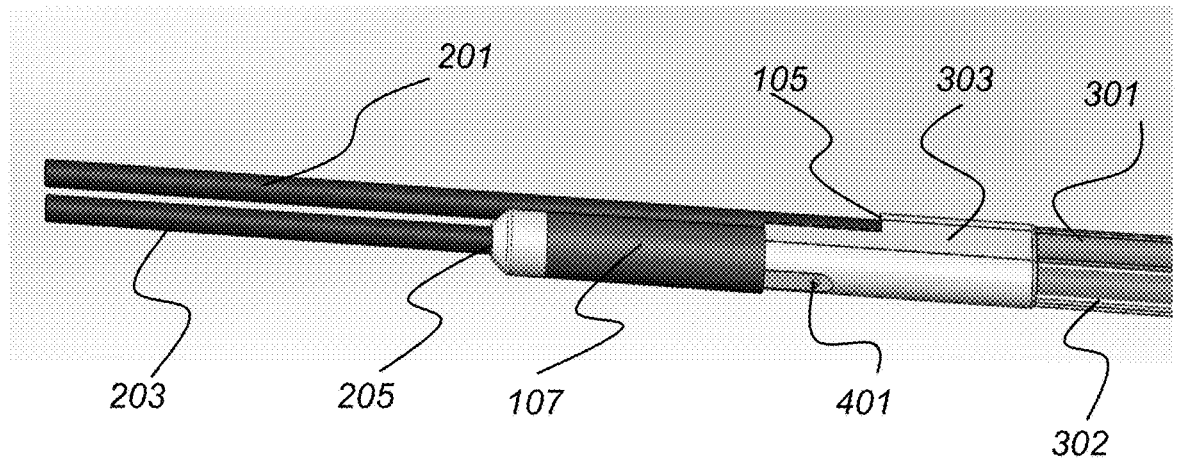
FIG. 5 shows a dual lumen imaging apparatus support with a functional measurement sensor.

Exit ports may be disposed at the same location along the catheter, imaging apparatus support, or dual lumen tracking tip, or may be offset or disposed on separate components on the catheter body. FIGS. 5-9 illustrate various embodiments of imaging apparatus supports. FIG. 5 shows a dual lumen imaging apparatus support 303 with a first guidewire lumen 301 and a second guidewire lumen 302 with a first guidewire 201 and a second guidewire 203 disposed therein. The imaging apparatus support 303 includes an imaging apparatus 107 with the second guidewire 203 and guidewire lumen 302 passing therethrough. The first exit port 105 is offset from the second exit port 205 and is proximal to the imaging apparatus 107 while the second exit port is distal to the imaging apparatus 107. The imaging apparatus support 303 further comprises a functional measurement sensor 401.

Figure 6:
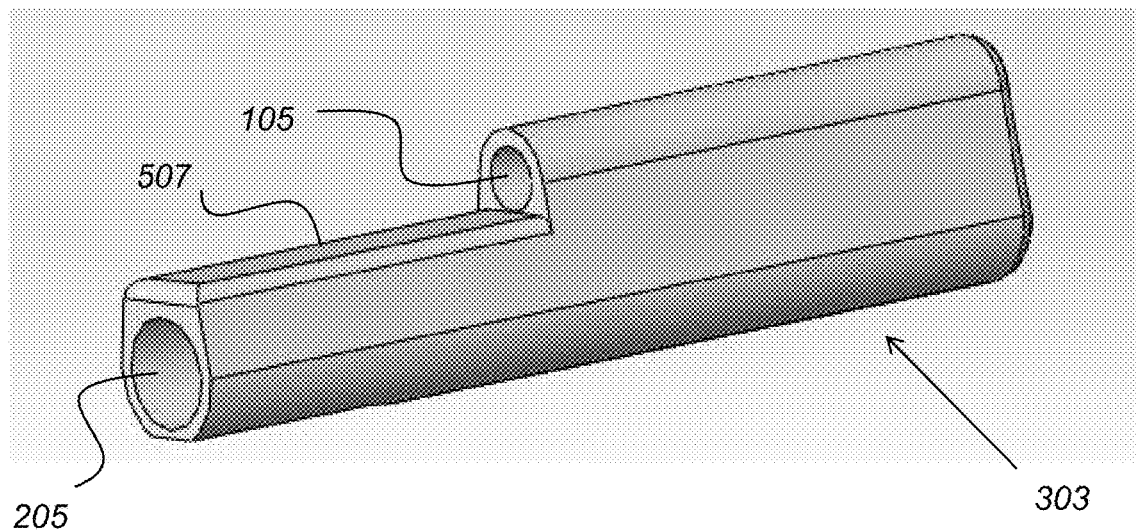
FIG. 6 shows a dual lumen imaging apparatus support with offset exit ports and a flattened surface after the proximal of the two exit ports.

FIG. 6 shows a dual lumen imaging apparatus support 303 with a first exit port 105 that is offset from and proximal to the second exit port 205. Additionally, the surface of the imaging apparatus support 303 after the first exit port 105 is flattened 507. The imaging apparatus support 303 further comprises a functional measurement sensor 401. In certain embodiments where an exit port is located proximal to the end of the catheter, tip, or transducer support, the surface of the catheter, tip, or transducer support distal to the exit port may be flattened as in FIG. 6. The flat surface 507, may provide structural support against guidewire or catheter kinking and/or may provide a mounting point for the transducer or imaging apparatus. An imaging apparatus may be mounted using, for example, a flex leg and adhesive or mechanical fasteners. A flattened mounting surface 507 may provide additional space for padding. Padding at the imaging apparatus mounting surface can mitigate the risk of physically induced image failure.

FIG. 7 illustrates an imaging apparatus support 303 with a first exit port 105 that is offset from and proximal to the second exit port 205. Additionally, the surface of the imaging apparatus support 303 after the first exit port 105 is flattened 507. The imaging apparatus support 303 further comprises a functional measurement sensor 401.

Figure 8:
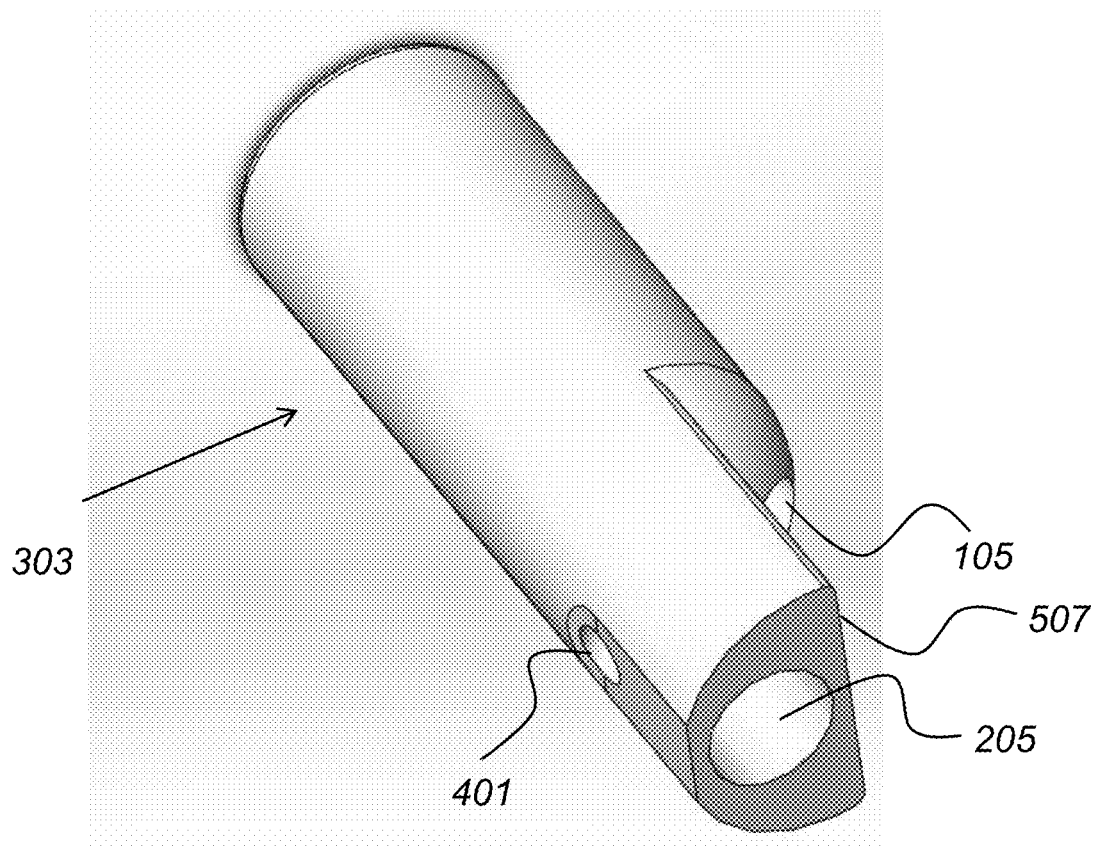
FIG. 8 shows a dual lumen imaging apparatus support with offset exit ports and rounded exit port and a functional measurement sensor.

Exit ports of the invention may be flat or perpendicular to the guidewire lumen which they terminate as illustrated by the second exit port 205 in FIG. 8. Exit ports may alternatively be rounded as shown by the first exit port 105 in FIG. 8 or angled relative to the catheter, guidewire lumens, tracking tip, or imaging apparatus support as shown by the first exit port 105 in FIG. 7. Angled or rounded exit ports may ease passage of the catheter through a body lumen. Exit ports may form an obtuse angle with a line tangential to the distal portion of the elongated body, imaging apparatus support, or tracking tip.

Figure 3:
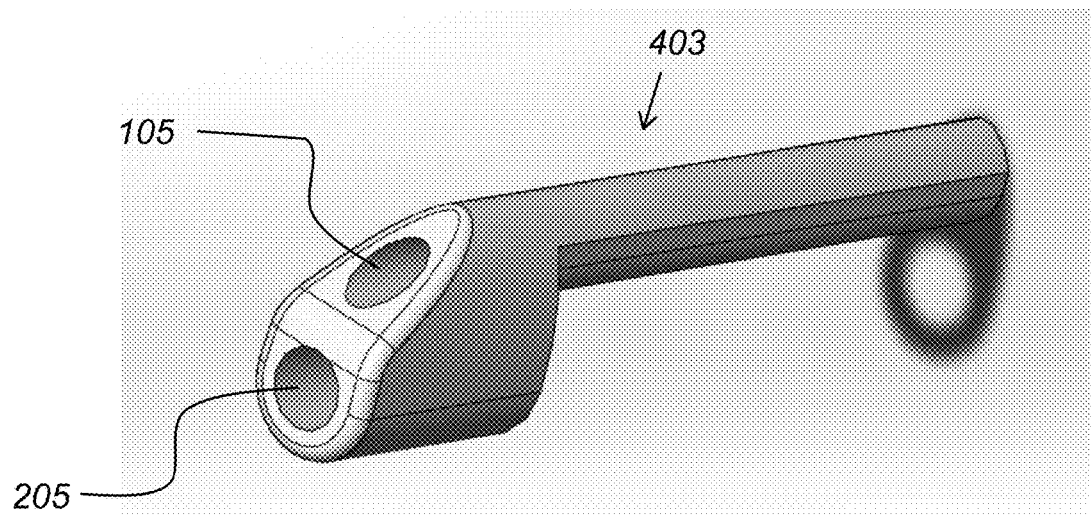
FIG. 3 shows a dual lumen tracking tip with imaging apparatus support.
Figure 4:
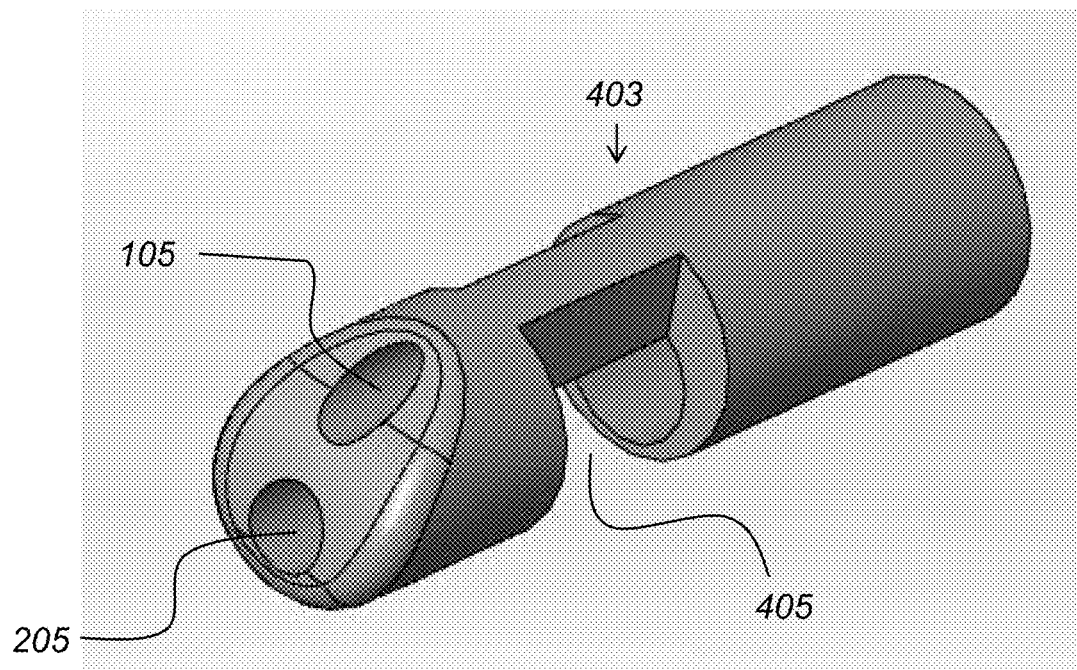
FIG. 4 shows a dual lumen tracking tip with an extended imaging apparatus support and a cut-out at the imaging plane of the imaging apparatus.

Exemplary embodiments of separate, dual lumen tracking tips 403 are shown in FIGS. 3 and 4. FIG. 3 shows a dual lumen tracking tip 403 with a first exit port 105 and a second exit port 205 disposed thereon. The first exit port 105 is angled relative to the second exit port 205 so that the tip presents a frontal surface are with reduced drag. FIG. 4 shows a dual lumen tracking tip 403 with a first exit port 105 and a second exit port 205 disposed thereon with a rounded frontal surface area. The dual lumen tracking tip 403 is configured to fully encase the imaging apparatus and includes a cutout 405 for the imaging plane of the imaging apparatus so that the tracking tip does not interfere with the intraluminal imaging. In various embodiments, dual lumen tracking tips may be used in conjunction with a dual lumen imaging apparatus support or an imaging apparatus may be coupled directly proximal or distal to the dual lumen tracking tip.

Figure 9:
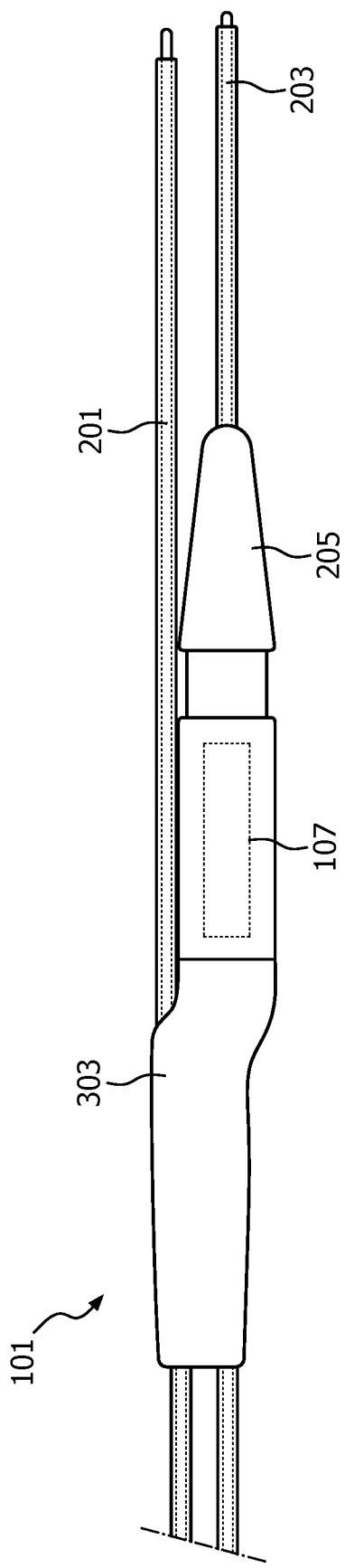
FIG. 9 shows a dual lumen imaging apparatus support with guidewires therethrough and a single lumen short tip.
Figure 10:
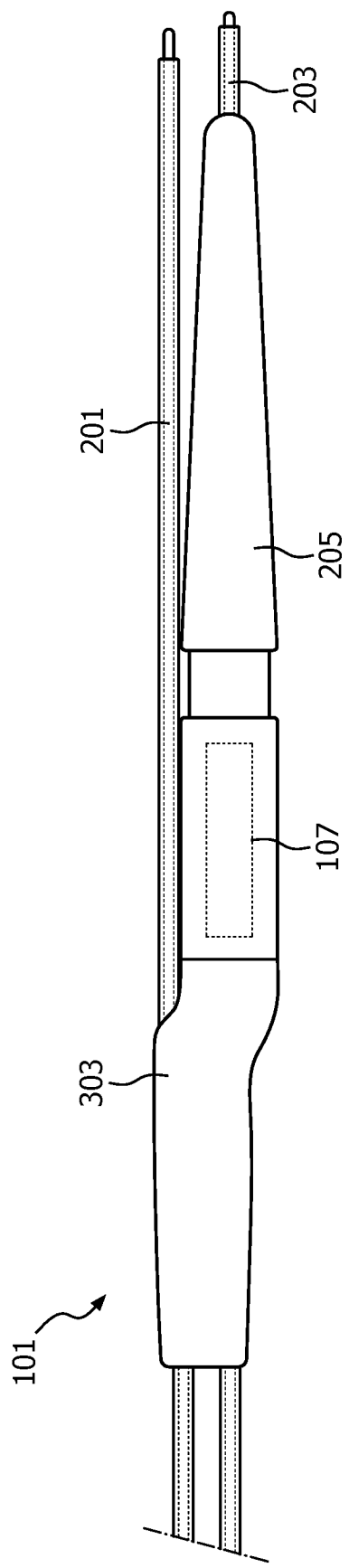
FIG. 10 shows a dual lumen imaging apparatus support with guidewires therethrough and a dual lumen extended tip.

Examples of dual lumen catheters are shown in FIGS. 9 and 10. FIG. 9 illustrates a dual lumen catheter 101 with a imaging apparatus 107 housed in an imaging apparatus support 303 and a separate tip 205. The second guidewire 203 travels through the imaging apparatus 107 and exits distally to the first guidewire 201. FIG. 10 illustrates a dual lumen catheter 101 with a imaging apparatus 107 housed in an imaging apparatus support 303 and an extended, integrated tip 205. The second guidewire 203 travels through the imaging apparatus 107 and exits distally to the first guidewire 201.

The proximal portion of the catheter may terminate at a hub such as a Y-arm, with, for instance, entry ports for the first and second catheter. A microcable coupled to the imaging apparatus at the distal portion of the catheter may emerge from a dedicated or shared purpose lumen at the proximal end of the catheter and may be coupled to a computer, a monitor, or other equipment configured to interpret and convey information from the imaging apparatus.

In certain aspects, the imaging apparatus may be coupled, through a microcable or otherwise, to a controller including a processor, or to a processor, to control and/or record data from the imaging apparatus. The controller will typically comprise computer hardware and/or software, often including one or more programmable processor units running machine readable program instructions or code for implementing some or all of one or more of the methods described herein. The code will often be embodied in a tangible media such as a memory (optionally a read only memory, a random access memory, a non-volatile memory, or the like) and/or a recording media (such as a floppy disk, a hard drive, a CD, a DVD, a non-volatile solid-state memory card, or the like). The code and/or associated data and signals may also be transmitted to or from the processor via a network connection, and some or all of the code may also be transmitted between components of catheter system and within the controller.

In certain embodiments, the controller may direct rotational or longitudinal movement of the imaging apparatus on the catheter body or on a drive cable. The controller can be configured to receive and display imaging data from the imaging apparatus and to coordinate intraluminal movements of the imaging apparatus while receiving data (e.g., in pull-back IVUS or pull-back OCT). Furthermore, the controller may also control movement and activation of the denervation assembly to facilitate placement of the denervation assembly in relation to the target tissue and delivery of denervation therapy to the target tissue. In certain embodiments, the controller may control deployment of an expandable member in order to bring a denervation assembly mounted thereon into contact with target tissue on the wall of the lumen (e.g., renal denervation in a renal artery).

In other embodiments, the imaging apparatus may rotate or translate using drive cables within the catheter body. Catheters having imaging assemblies that rotate and translate are known generally as "pull-back" catheters. The principles of pull-back OCT are described in detail in U.S. Pat. No. 7,813,609 and US Patent Publication No. 20090043191, both of which are incorporated herein by reference in their entireties. The mechanical components, including drive shafts, rotating interfaces, windows, and couplings, are similar between the various forms of pull-back imaging.

In various embodiments, the imaging apparatus may be integrated within the body of the catheter, may circumscribe the catheter, may be placed on a distal end face of the catheter, and/or may run along the body of the catheter. The catheter may also include an outer support structure or coating surrounding the imaging apparatus.

The guidewire lumens of the dual lumen imaging apparatus may be fixed relative to each other and the imaging apparatus. Alternatively, one or more of the guidewire lumens may be moveable relative to the imaging apparatus, each other, or both so that the relative position of the first and/or second exit ports to the imaging apparatus may be altered by extending or retracting a guidewire lumen out of or into the catheter body.

In certain aspects, the first guidewire lumen may comprise a spring loaded needle OTW lumen. The spring loaded needle lumen may be constructed from a material such as stainless steel or nitinol. The spring loaded needle may be controllable from the proximal end of the device. Any of the first exit port 105 configurations shown in FIGS. 12A-12D may be incorporated independently or in combination into a dual lumen imaging apparatus. For example, a spring loaded first guidewire lumen 301 may be movable in relation to a dual lumen imaging apparatus support 303 so that the position of the first exit port 105 may be varied in relation to the imaging apparatus 107 by advancing or withdrawing the first guidewire lumen 301 with respect to the imaging apparatus support 303. Where the first guidewire lumen 301 comprises a needle lumen, the first exit port 105 may be sharp and/or beveled to allow insertion into tissue or occlusive material.

In certain embodiments, the entire needle lumen or sections of it may be uniformly or variably laser cut or braided to improve flexibility and ease advancement of the catheter through a body lumen. In certain embodiments, the first guidewire lumen 301 may include a pre-bent portion 153 which may be accomplished, for example, through use of a shape-memory material such as nitinol. A pre-bent portion 153 may comprise a variety of angles such as less than 1 degree, or 1, 5, 10, 15, 20, 25, 30, 35, 40, 45, 50, 55, 60, 70, 80, 90, or more degrees. In preferred embodiments, the pre-bent portion 153 comprises an angle of 90 degrees or less to ease retraction of the first guidewire lumen into the imaging apparatus support 303 after use and before withdraw of the catheter from the body lumen.

Figure 12A:
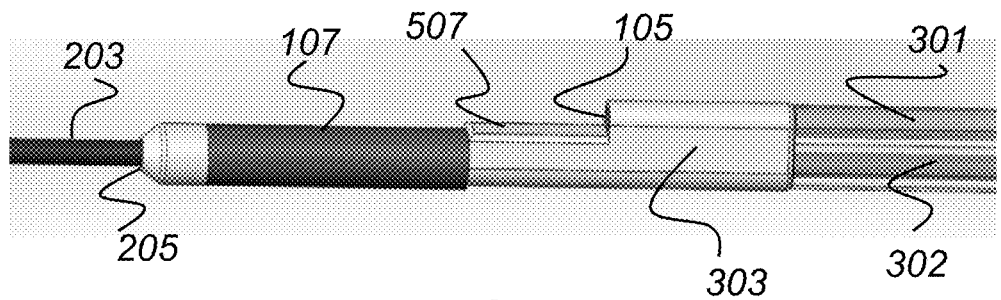
FIGS. 12A-12D show dual lumen imaging apparatuses with a first exit port having various configurations relative to an imaging apparatus.
Figure 12B:
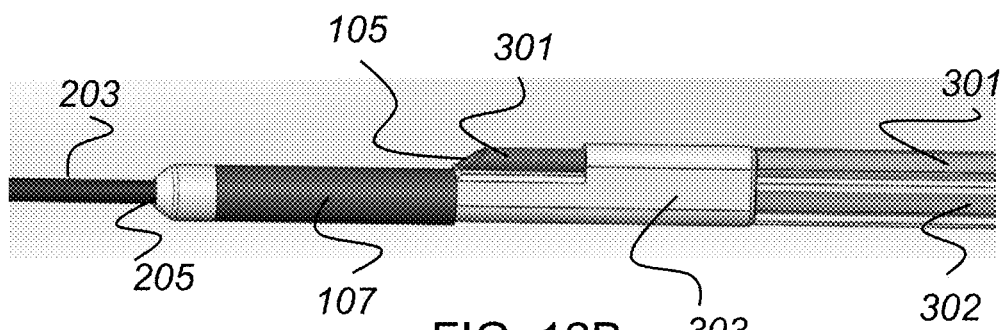
Figure 12C:
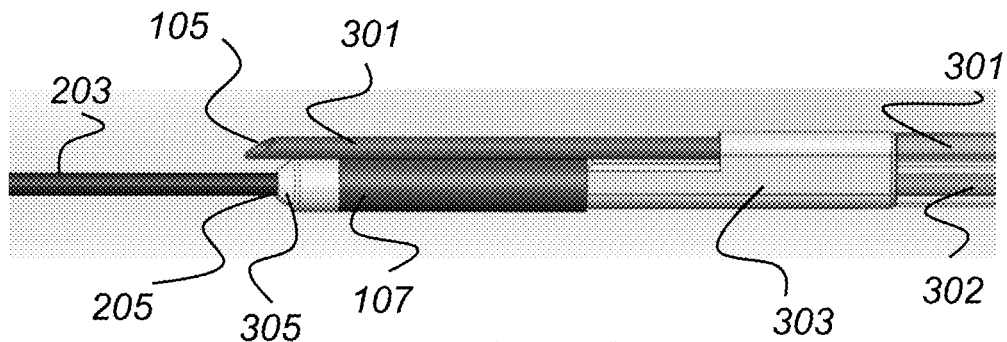
Figure 12D:
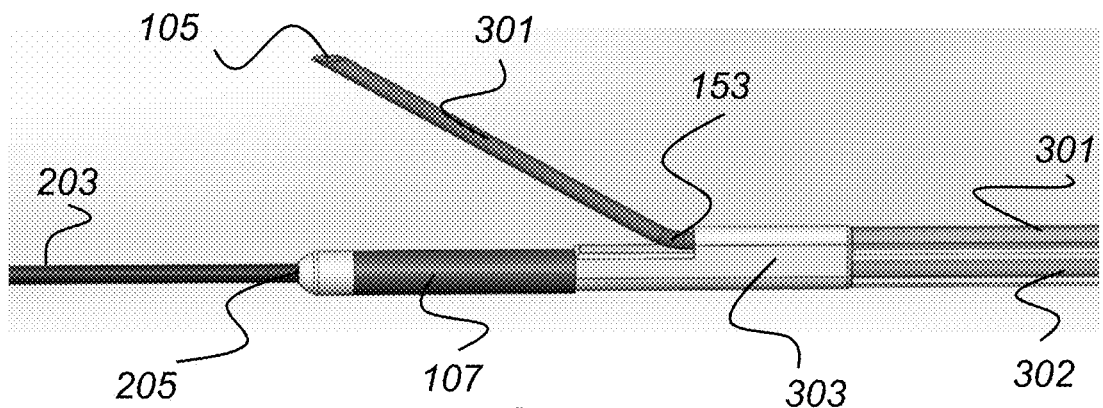

In various embodiments, the catheter body may comprise a material with greater rigidity than the first guidewire lumen 301 so that, when withdrawn into the imaging apparatus support 303 and catheter body, the first guidewire lumen remains approximately parallel to the catheter body and the second guidewire lumen 303 as shown in FIGS. 12A-12C; but when the first guidewire lumen 301 is extended so that the pre-bent portion 153 is beyond the imaging apparatus support 303, the first guidewire lumen 301 assumes the angle of the pre-bent portion 153 as shown in FIG. 12D. The length of the guidewire lumen 301 distal to the pre-bent portion 153 may be configured along with the angle of the pre-bent portion 153 in order to achieve a variety of orientations of the first exit port 105 relative to the imaging apparatus support 303. In certain aspects the first guidewire lumen 301 may have multiple pre-bent portions 153 spaced at various lengths along the distal end of the first guidewire lumen 301 so that the angle of the first guidewire lumen 301 relative to the catheter body may be increased in steps by advancing one or more pre-bent portions 153 beyond the distal end of the imaging apparatus support 303. The use of multiple discrete pre-bent portions 153 may also be used to achieve a cumulative angle greater than 90 degrees without introducing problems with retraction of the first guidewire lumen 301 into the into the imaging apparatus support 303 after use and before withdraw of the catheter from the body lumen. In certain embodiments the location of the first exit port 105 may be further modified through axial rotation of the first guidewire lumen 301 after the pre-bent portion 153 has been extended beyond the distal opening of the imaging apparatus support 303.

FIG. 12A shows a dual lumen imaging apparatus support 303 with an imaging apparatus 107 second guidewire lumen 302 passing therethrough. An RX guidewire 203 emerges from the second exit port 205, distal to the imaging apparatus 107. The first guidewire lumen 301 comprises a first exit port 105 that is disposed proximal to the imaging apparatus 303 by a distance. The surface of the imaging apparatus support 303 after the first exit port 105 is flattened 507.

FIG. 12B shows a dual lumen imaging apparatus support 303 with an imaging apparatus 107 second guidewire lumen 302 passing therethrough. An RX guidewire 203 emerges from the second exit port 205, distal to the imaging apparatus 107. The first guidewire lumen 301 comprises a first exit port 105 that is disposed at the proximal edge of the imaging apparatus 303.

FIG. 12C shows a dual lumen imaging apparatus support 303 with an imaging apparatus 107 second guidewire lumen 302 passing therethrough. An RX guidewire 203 emerges from the second exit port 205, distal to the imaging apparatus 107. The first guidewire lumen 301 comprises a first exit port 105 that is disposed distal to the imaging apparatus 107 and at or just distal to the tip 305 and the second exit port 205.

FIG. 12D shows a dual lumen imaging apparatus support 303 with an imaging apparatus 107 second guidewire lumen 302 passing therethrough. An RX guidewire 203 emerges from the second exit port 205, distal to the imaging apparatus 107. The first guidewire lumen 301 is angled from the imaging apparatus 107 by a pre-bent portion 153.

In certain embodiments, a device of the invention may include one or more perfusion holes disposed along the device. Perfusion holes may be disposed along the OTW lumen. Perfusion holes can be perpendicular to the OTW lumen or angled. Perfusion holes 167 may be disposed on the catheter tip, along the catheter body or on a dual lumen imaging apparatus support 303 as shown in FIG. 13 or 15-17. Perfusion holes 167 may be disposed proximal to the imaging apparatus 107 and the first 105 and second 205 exit ports and may be disposed on one side of the catheter of imaging apparatus support 303 or may be disposed on multiple sides along the outer surface of the catheter of imaging apparatus support 303.

Imaging Apparatus

In certain embodiments, the imaging and treatment device of the invention includes an imaging apparatus. The imaging apparatus may be disposed on the catheter body, an imaging apparatus support at the distal end of a catheter body, or on a drive cable depending on the imaging technology being employed. Any imaging apparatus may be used with devices and methods of the invention, such as optical-acoustic imaging apparatus, intravascular ultrasound (IVUS) or optical coherence tomography (OCT). The imaging apparatus is used to send and receive signals to and from the imaging surface that form the imaging data.

In some embodiments, the imaging apparatus is an IVUS imaging apparatus. The imaging apparatus can be a phased-array IVUS imaging apparatus, a pull-back type IVUS imaging apparatus, including rotational IVUS imaging assemblies, or an IVUS imaging apparatus that uses photoacoustic materials to produce diagnostic ultrasound and/or receive reflected ultrasound for diagnostics. IVUS imaging assemblies and processing of IVUS data are described for example in Yock, U.S. Pat. Nos. 4,794,931, 5,000,185, and 5,313,949; Sieben et al., U.S. Pat. Nos. 5,243,988, and 5,353,798; Crowley et al., U.S. Pat. No. 4,951,677; Pomeranz, U.S. Pat. No. 5,095,911, Griffith et al., U.S. Pat. No. 4,841,977, Maroney et al., U.S. Pat. No. 5,373,849, Born et al., U.S. Pat. No. 5,176,141, Lancee et al., U.S. Pat. No. 5,240,003, Lancee et al., U.S. Pat. No. 5,375,602, Gardineer et at., U.S. Pat. No. 5,373,845, Eberle et al., U.S. Pat. No. 5,453,575, Eberle et al., U.S. Pat. No. 5,368,037, Eberle et at., U.S. Pat. No. 5,183,048, Eberle et al., U.S. Pat. No. 5,167,233, Eberle et at., U.S. Pat. No. 4,917,097, Eberle et at., U.S. Pat. No. 5,135,486, and other references well known in the art relating to intraluminal ultrasound devices and modalities. All of these references are incorporated by reference herein in their entirety.

IVUS imaging is widely used as a diagnostic tool for assessing a diseased vessel, such as an artery, within the human body to determine the need for treatment, to guide an intervention, and/or to assess its effectiveness. An IVUS device including one or more ultrasound transducers is introduced into the vessel and guided to the area to be imaged. The transducers emit and then receive backscattered ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a 360 degree cross-sectional image of the vessel where the device is placed.

There are two general types of IVUS devices in use today: rotational and solid-state (also known as synthetic aperture phased array). For a typical rotational IVUS device, a single ultrasound transducer assembly is located at the tip of a flexible driveshaft that spins inside a plastic sheath inserted into the vessel of interest. The transducer assembly is oriented such that the ultrasound beam propagates generally perpendicular to the axis of the device. The fluid-filled sheath protects the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning echoes reflected from various tissue structures. The IVUS imaging system assembles a two dimensional display of the vessel cross-section from a sequence of pulse/acquisition cycles occurring during a single revolution of the transducer. Suitable rotational IVUS catheters include, for example the REVOLUTION 45 MHz catheter (offered by the Volcano Corporation).

In contrast, solid-state IVUS devices carry a transducer complex that includes an array of ultrasound transducers distributed around the circumference of the device connected to a set of transducer controllers. The transducer controllers select transducer sets for transmitting an ultrasound pulse and for receiving the echo signal. By stepping through a sequence of transmit-receive sets, the solid-state IVUS system can synthesize the effect of a mechanically scanned transducer element but without moving parts. The same transducer elements can be used to acquire different types of intravascular data. The different types of intravascular data are acquired based on different manners of operation of the transducer elements. The solid-state scanner can be wired directly to the imaging system with a simple electrical cable and a standard detachable electrical connector.

The transducer subassembly can include either a single transducer or an array. The transducer elements can be used to acquire different types of intravascular data, such as flow data, motion data and structural image data. For example, the different types of intravascular data are acquired based on different manners of operation of the transducer elements. For example, in a gray-scale imaging mode, the transducer elements transmit in a certain sequence one gray-scale IVUS image. Methods for constructing IVUS images are well-known in the art, and are described, for example in Hancock et al. (U.S. Pat. No. 8,187,191), Nair et al. (U.S. Pat. No. 7,074,188), and Vince et al. (U.S. Pat. No. 6,200,268), the content of each of which is incorporated by reference herein in its entirety. In flow imaging mode, the transducer elements are operated in a different way to collect the information on the motion or flow. This process allows one image (or frame) of flow data to be acquired. The particular methods and processes for acquiring different types of intravascular data, including operation of the transducer elements in the different modes (e.g., gray-scale imaging mode, flow imaging mode, etc.) consistent with the present invention are further described in U.S. patent application Ser. No. 14/037,683, the content of which is incorporated by reference herein in its entirety.

The acquisition of each flow frame of data is interlaced with an IVUS gray scale frame of data. Operating an IVUS catheter to acquire flow data and constructing images of that data is further described in O'Donnell et al. (U.S. Pat. No. 5,921,931), U.S. Provisional Patent Application No. 61/587,834, and U.S. Provisional Patent Application No. 61/646,080, the content of each of which is incorporated by reference herein its entirety. Commercially available fluid flow display software for operating an IVUS catheter in flow mode and displaying flow data is ChromaFlo® (IVUS fluid flow display software offered by the Volcano Corporation). Suitable phased array imaging assemblies are found on Volcano Corporation's EAGLE EYE Platinum Catheter, EAGLE EYE Platinum Short-Tip Catheter, and EAGLE-EYE Gold Catheter. Catheters and imaging apparatuses of the invention may be compatible with automated body lumen measurement software such as VH® IVUS (Volcano Corporation, San Diego, Calif.), image highlighting software for blood, plague and software for correlating a single view from IVUS and angiogram images such as SyncVision™ (Volcano Corporation, San Diego, Calif.).

In addition to IVUS, other intraluminal imaging technologies may be suitable for use in methods of the invention for assessing and characterizing vascular access sites in order to diagnose a condition and determine appropriate treatment. For example, an Optical Coherence Tomography (OCT) catheter may be used to obtain intraluminal images in accordance with the invention. OCT is a medical imaging methodology using a miniaturized near infrared light-emitting probe. As an optical signal acquisition and processing method, it captures micrometer-resolution, three-dimensional images from within optical scattering media (e.g., biological tissue). Recently it has also begun to be used in interventional cardiology to help diagnose coronary artery disease. OCT allows the application of interferometric technology to see from inside, for example, blood vessels, visualizing the endothelium (inner wall) of blood vessels in living individuals.

OCT systems and methods are generally described in Castella et al., U.S. Pat. No. 8,108,030, Milner et al., U.S. Patent Application Publication No. 2011/0152771, Condit et al., U.S. Patent Application Publication No. 2010/0220334, Castella et al., U.S. Patent Application Publication No. 2009/0043191, Milner et al., U.S. Patent Application Publication No. 2008/0291463, and Kemp, N., U.S. Patent Application Publication No. 2008/0180683, the content of each of which is incorporated by reference in its entirety.

OCT is a medical imaging methodology using a miniaturized near infrared light-emitting probe. As an optical signal acquisition and processing method, it captures micrometer-resolution, three-dimensional images from within optical scattering media (e.g., biological tissue). Recently it has also begun to be used in interventional cardiology to help diagnose coronary artery disease. OCT allows the application of interferometric technology to see from inside, for example, blood vessels, visualizing the endothelium (inner wall) of blood vessels in living individuals.

OCT systems and methods are generally described in Castella et al., U.S. Pat. No. 8,108,030, Milner et al., U.S. Patent Application Publication No. 2011/0152771, Condit et al., U.S. Patent Application Publication No. 2010/0220334, Castella et al., U.S. Patent Application Publication No. 2009/0043191, Milner et al., U.S. Patent Application Publication No. 2008/0291463, and Kemp, N., U.S. Patent Application Publication No. 2008/0180683, the content of each of which is incorporated by reference in its entirety.

In OCT, a light source delivers a beam of light to an imaging device to image target tissue. Light sources can include pulsating light sources or lasers, continuous wave light sources or lasers, tunable lasers, broadband light source, or multiple tunable laser. Within the light source is an optical amplifier and a tunable filter that allows a user to select a wavelength of light to be amplified. Wavelengths commonly used in medical applications include near-infrared light, for example between about 800 nm and about 1700 nm.

Aspects of the invention may obtain imaging data from an OCT system, including OCT systems that operate in either the time domain or frequency (high definition) domain. Basic differences between time-domain OCT and frequency-domain OCT is that in time-domain OCT, the scanning mechanism is a movable mirror, which is scanned as a function of time during the image acquisition. However, in the frequency-domain OCT, there are no moving parts and the image is scanned as a function of frequency or wavelength.

In time-domain OCT systems an interference spectrum is obtained by moving the scanning mechanism, such as a reference mirror, longitudinally to change the reference path and match multiple optical paths due to reflections within the sample. The signal giving the reflectivity is sampled over time, and light traveling at a specific distance creates interference in the detector. Moving the scanning mechanism laterally (or rotationally) across the sample produces two-dimensional and three-dimensional images.

In frequency domain OCT, a light source capable of emitting a range of optical frequencies excites an interferometer, the interferometer combines the light returned from a sample with a reference beam of light from the same source, and the intensity of the combined light is recorded as a function of optical frequency to form an interference spectrum. A Fourier transform of the interference spectrum provides the reflectance distribution along the depth within the sample.

Several methods of frequency domain OCT are described in the literature. In spectral-domain OCT (SD-OCT), also sometimes called "Spectral Radar" (Optics letters, Vol. 21, No. 14 (1996) 1087-1089), a grating or prism or other means is used to disperse the output of the interferometer into its optical frequency components. The intensities of these separated components are measured using an array of optical detectors, each detector receiving an optical frequency or a fractional range of optical frequencies. The set of measurements from these optical detectors forms an interference spectrum (Smith, L. M. and C. C. Dobson, Applied Optics 28: 3339-3342), wherein the distance to a scatterer is determined by the wavelength dependent fringe spacing within the power spectrum. SD-OCT has allowed the determination of distance and scattering intensity of multiple scatters lying along the illumination axis by analyzing a single the exposure of an array of optical detectors so that no scanning in depth is necessary. Typically the light source emits a broad range of optical frequencies simultaneously.

Alternatively, in swept-source OCT, the interference spectrum is recorded by using a source with adjustable optical frequency, with the optical frequency of the source swept through a range of optical frequencies, and recording the interfered light intensity as a function of time during the sweep. An example of swept-source OCT is described in U.S. Pat. No. 5,321,501.

Generally, time domain systems and frequency domain systems can further vary in type based upon the optical layout of the systems: common beam path systems and differential beam path systems. A common beam path system sends all produced light through a single optical fiber to generate a reference signal and a sample signal whereas a differential beam path system splits the produced light such that a portion of the light is directed to the sample and the other portion is directed to a reference surface. Common beam path systems are described in U.S. Pat. Nos. 7,999,938; 7,995,210; and U.S. Pat. No. 7,787,127 and differential beam path systems are described in U.S. Pat. Nos. 7,783,337; 6,134,003; and 6,421,164, the contents of each of which are incorporated by reference herein in its entirety.

In certain embodiments, angiogram image data is obtained simultaneously with the imaging data obtained from the imaging apparatus and/or imaging guidewire of the present invention. In such embodiments, the catheter and/or guidewire may include one or more radiopaque labels that allow for co-locating image data with certain positions on a vasculature map generated by an angiogram. Co-locating intraluminal image data and angiogram image data is known in the art, and described in U.S. Publication Nos. 2012/0230565, 2011/0319752, and 2013/0030295.

In certain embodiments, the imaging apparatus may be an optical-acoustic imaging apparatus. Optical-acoustic imaging apparatuses include at least one imaging element to send and receive imaging signals. In one embodiment, the imaging apparatus includes at least one acoustic-to-optical transducer. In certain embodiments, the acoustic-to-optical transducer is a Fiber Bragg Grating within an optical fiber. In addition, the imaging assemblies may include the optical fiber with one or more Fiber Bragg Gratings (acoustic-to-optical transducer) and one or more other transducers. The at least one other transducer may be used to generate the acoustic energy for imaging. Acoustic generating transducers can be electric-to-acoustic transducers or optical-to-acoustic transducers. The imaging assemblies suitable for use in devices of the invention are described in more detail below.

Fiber Bragg Gratings for imaging provides a means for measuring the interference between two paths taken by an optical beam. A partially-reflecting Fiber Bragg Grating is used to split the incident beam of light into two parts, in which one part of the beam travels along a path that is kept constant (constant path) and another part travels a path for detecting a change (change path). The paths are then combined to detect any interference in the beam. If the paths are identical, then the two paths combine to form the original beam. If the paths are different, then the two parts will add or subtract from each other and form an interference. The Fiber Bragg Grating elements are thus able to sense a change wavelength between the constant path and the change path based on received ultrasound or acoustic energy. The detected optical signal interferences can be used to generate an image using any conventional means.

In certain embodiments, the imaging apparatus includes a piezoelectric element to generate the acoustic or ultrasound energy. In such aspect, the optical fiber of the imaging apparatus may by coated by the piezoelectric element. The piezoelectric element may include any suitable piezoelectric or piezoceramic material. In one embodiment, the piezoelectric element is a poled polyvinylidene fluoride or polyvinylidene difluoride material. The piezoelectric element can be connected to one or more electrodes that are connected to a generator that transmits pulses of electricity to the electrodes. The electric pulses cause mechanical oscillations in the piezoelectric element, which generates an acoustic signal. Thus, the piezoelectric element is an electric-to-acoustic transducer. Primary and reflected pulses (i.e. reflected from the imaging medium) are received by the Bragg Grating element and transmitted to an electronic instrument to generate an imaging.

In some embodiments, the imaging apparatus includes an optical fiber with Fiber Bragg Grating and a piezoelectric element. In this embodiment, an electrical generator stimulates the piezoelectric element (electrical-to-acoustic transducer) to transmit ultrasound impulses to both the Fiber Bragg Grating and the outer medium in which the device is located. For example, the outer medium may include blood when imaging a vessel. Primary and reflected impulses are received by the Fiber Bragg Grating (acting as an acoustic-to-optical transducer). The mechanical impulses deform the Bragg Grating and cause the Fiber Bragg Grating to modulate the light reflected within the optical fiber, which generates an interference signal. The interference signal is recorded by electronic detection instrument, using conventional methods. The electronic instrument may include a photodetector and an oscilloscope. An image can be generated from these recorded signals. The electronic instruments modulation of light reflected backwards from the optical fiber due to mechanical deformations. The optical fiber with a Bragg Grating described herein, the imaging apparatus described herein and other varying embodiments are described in more detail in U.S. Pat. Nos. 6,659,957 and 7,527,594 and in U.S. Patent Publication No. 2008/0119739.

In another aspect, the imaging apparatus does not require an electrical-to-acoustic transducer to generate acoustic/ultrasound signals. Instead, the imaging apparatus utilizes the one or more Fiber Bragg Grating elements of the optical fiber in combination with an optical-to-acoustic transducer material to generate acoustic energy from optical energy. In this aspect, the acoustic-to-optical transducer (signal receiver) also acts as an optical-to-acoustic transducer (signal generator).

To generate the acoustic energy, imaging apparatus may include a combination of blazed and unblazed Fiber Bragg Gratings. Unblazed Bragg Gratings typically include impressed index changes that are substantially perpendicular to the longitudinal axis of the fiber core of the optical fiber. Unblazed Bragg Gratings reflect optical energy of a specific wavelength along the longitudinal of the optical fiber. Blazed Bragg Gratings typically include obliquely impressed index changes that are at a non-perpendicular angle to the longitudinal axis of the optical fiber. Blazed Bragg Gratings reflect optical energy away from the longitudinal axis of the optical fiber.

One or more imaging assemblies may be incorporated into an imaging guidewire or the catheter to allow an operator to image a luminal surface. The one or more imaging assemblies of the imaging guidewire or catheter are referred to generally as an imaging apparatus. In some embodiments, instead of presenting one 2-D slice of the anatomy, the system is operated to provide a 3-D visual image that permits the viewing of a desired volume of the patient's anatomy or other imaging region of interest. This allows the physician to quickly see the detailed spatial arrangement of structures, such as lesions, with respect to other anatomy.

In some aspects, the transducers may comprise capacitive micromachined ultrasonic transducers (CMUTs). CMUTs, which uses micromachining technology, allows for miniaturize device dimensions and produces capacitive transducers that perform comparably to the piezoelectric counterparts. CMUTs are essentially capacitors with one moveable electrode. If an alternating voltage is applied to the device then the moveable electrode begins to vibrate, thus causing ultrasound to be generated. If the CMUTs are used as receivers, then changes in pressure such as those from an ultrasonic wave cause the moveable electrode to deflect and hence produce a measurable change in capacitance. CMUT arrays can be made in any arbitrary geometry with very small dimensions using photolithographic techniques and standard microfabrication processes.

In some aspects, the transducers may comprise piezoelectric micromachined ultrasonic transducers (pMUTs), which are based on the flexural motion of a thin membrane coupled with a thin piezoelectric film. It should be noted that pMUTs exhibit superior bandwidth and offer considerable design flexibility, which allows for operation frequency and acoustic impedance to be tailored for numerous applications.

Methods

Catheters of the invention may be used to access various healthy and diseased body lumens and, in particular, lumens of the vasculature. The real-time images obtained may be used to locate a region or location of interest within a body lumen and to guide and observe the delivery and after-effect of various treatments. Regions of interest are typical regions that include a defect or tissues requiring treatment. The devices and methods, however, are also suitable for treating stenosis of body lumens and other hyperplastic and neoplastic conditions in other body lumens, such as the ureter, the biliary duct, respiratory passages, the pancreatic duct, the lymphatic duct, and the like. In addition, the region of interest can include, for example, a location for stent placement or a location including plaque or diseased tissue that needs to be removed or treated. In some instances, the region of interest may include the renal artery where renal denervation therapy may be applied to the afferent and efferent nerves therein.

Catheters of the invention may be used in combination with a variety of treatment methods to treat a variety of vascular problems. In certain aspects, the catheter may serve as a delivery catheter, ablation catheter, extraction catheter or energizing catheter to perform an intraluminal procedure. The catheter may include a denervation assembly to perform an intraluminal procedure. An OTW guidewire lumen may act as a utility lumen while an additional RX lumen acts as a delivery lumen, or vice versa. In some embodiments, methods can include treating a chronic total occlusion. In catheters including a functional measurement sensor, the sensor may be used in combination with or independent of the imaging apparatus to verify position of the distal portion of the body at the chronic total occlusion by, for example, sensing a change in pressure. The first guidewire for support while crossing the chronic total occlusion and a therapy may be delivered to the chronic total occlusion through the second guidewire lumen while imaging local to the first and second exit ports from the imaging apparatus informs the procedure.

During a procedure, the imaging apparatus may be used to image cross-sections of the luminal surface and to visualize the position of one or more exit ports. In addition, the catheter may also include forward or distal facing imaging assemblies to image the luminal space and/or any procedure in front of or distal to the catheter. For example, the imaging apparatus can axially image a luminal surface for the location and selection of a region of interest suspected of containing afferent and efferent nerves for the accurate and targeted delivery of a treatment. This greatly improves visualization during the procedure by allowing an operator to have real-time images of the vessel wall while the denervation assembly of the catheter is engaged with that portion of the vessel wall. After the treatment procedure, the imaging apparatus of the catheter can be used to perform a final visualization of the luminal surface before the catheter is removed from the patient.

The devices of the invention may include static imaging assemblies that do not move with respect to the catheter body, or moving imaging assemblies. For example, the imaging apparatus may be a phased array of ultrasonic transducers for IVUS imaging, or a collection of CCD arrays. An array of assemblies will typically cover a circumference of the catheter to provide a 360° view of the lumen.

Catheters of the invention may be used to deliver intravascular treatment. In certain embodiments, one of the guidewire lumens may be used for stability or to provide support while another guidewire is removed or advanced through the other guidewire lumen. For example, the catheter may reach, along a first guidewire in a first guidewire lumen, a bifurcation in the vasculature, observable via the imaging apparatus on the distal portion of the catheter. After observing the bifurcation and determining a desired route, a user may select a shaped guidewire, less rigid than the first guidewire, to insure access to the desired branch of the bifurcation. The shaped guidewire may by advanced through the second guidewire lumen while the first guidewire maintains support of the catheter, out of the second exit port and into the desired branch at which point the first guidewire be retracted slightly allowing the catheter to follow the shape of the second, shaped guidewire and the catheter can be advanced into the desired branch.

Other embodiments of catheters and systems of using them, not disclosed herein, will be evident to those of skill in the art, and are intended to be covered by the claims listed below.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. An intravascular treatment catheter comprising:
an elongated body having a distal portion and a proximal portion, wherein the distal portion comprises an imaging apparatus support, wherein the imaging apparatus support comprises a first distal surface and a second distal surface, wherein the second distal surface is disposed distally of the first distal surface;
an imaging apparatus disposed at the distal portion of the body and disposed distally of the first distal surface and proximally of the second distal surface of the imaging apparatus support and having a channel passing therethrough, wherein the imaging apparatus is configured to image a location within a vasculature;
a first guidewire lumen comprising a first forward facing exit port formed in the first distal surface of the imaging apparatus support proximal to the imaging apparatus, wherein the first guidewire lumen extends substantially through the elongated body to receive an over the wire (OTW) guidewire that extends out of the first forward facing exit port proximal to the imaging apparatus; and
a second guidewire lumen, substantially parallel to the first guidewire lumen and extending through a distal portion of the elongated body to receive a rapid exchange (RX) guidewire while the OTW guidewire is present within the first guidewire lumen, wherein the second guidewire lumen comprises a second forward facing exit port disposed at the second distal surface of the imaging apparatus support, wherein the second exit port is disposed distally of the first exit port opposite the imaging apparatus from the first forward facing exit port, and wherein the second guidewire lumen extends through the channel of the imaging apparatus so that the RX guidewire extends out of the second forward facing exit port distal to the imaging apparatus and substantially parallel to the OTW guidewire extending out of the first forward facing exit port.

2. The intravascular treatment catheter of claim 1 wherein the imaging apparatus comprises an ultrasound transducer.

3. The intravascular treatment catheter of claim 1, further comprising a functional measurement sensor disposed proximally of the imaging apparatus.

4. The intravascular treatment catheter of claim 3 wherein the functional measurement sensor comprises at least one of a pressure sensor, a velocity sensor, a Doppler velocity sensor, and an optical sensor.

5. The intravascular treatment catheter of claim 1 wherein the first exit port and the second exit port are offset from each other on opposite sides of the imaging apparatus so that an imaging field of the imaging apparatus captures both the first and second exit ports.

6. The intravascular treatment catheter of claim 1 wherein the first and second exit ports are disposed within 5 cm of the imaging apparatus on the distal portion of the body.

7. The intravascular treatment catheter of claim 1 wherein the first distal surface forms an obtuse angle with a line tangential to the distal portion of the elongated body.

8. The intravascular treatment catheter of claim 1, configured to transmit axial torque applied at the proximal portion of the body to the distal portion of the body.

9. The intravascular treatment catheter of claim 8, further comprising a shaft, a braided material, or a coiled material for axial torque transmission.

10. The intravascular treatment catheter of claim 1 wherein the imaging apparatus is disposed around the second guidewire lumen.

11. The intravascular treatment catheter of claim 1 further comprising a pattern on the distal portion of the body wherein the pattern is configured to show an orientation of the distal portion of the body under x-ray imaging.

12. The intravascular treatment catheter of claim 1, further comprising a third lumen and a microcable disposed therethrough, said microcable extending from the imaging apparatus to the proximal portion of the catheter and in electronic communication with the imaging apparatus.

13. The intravascular treatment catheter of claim 1 wherein the first distal surface is angled relative to the second distal surface.

14. The intravascular treatment catheter of claim 1 wherein the first distal and the second distal surface form a rounded frontal surface area.

15. An intravascular treatment catheter system for insertion into a vasculature of a patient, the system comprising:
a first guidewire;
a second guidewire;

an elongated body having a distal portion and a proximal portion, wherein the distal portion comprises an imaging apparatus support, wherein the imaging apparatus support comprises first and second surfaces near the distal end of the elongated body, wherein the first and second surfaces are substantially parallel to each other but are spaced apart so that the first surface is proximal to the second surface;

an imaging apparatus disposed on the imaging apparatus support at the distal portion of the elongated body distal to the first distal surface and proximal to the second surface of the imaging apparatus support and having a channel passing therethrough, wherein the imaging apparatus has an imaging field that encompasses the first and second surfaces;

a first guidewire lumen extending substantially through the elongated body to a first forward facing exit port formed in the first surface of the imaging apparatus support proximal to the imaging apparatus to receive the first guidewire so that the first guidewire extends out of the first forward facing exit port proximal to the imaging apparatus; and a second guidewire lumen extending substantially parallel to the first guidewire lumen through the elongate body, the second guidewire lumen extending through the channel of the imaging apparatus to a second forward facing exit port at the second surface of the imaging apparatus support so that the second guidewire extends out of the second forward facing exit port distal to the imaging apparatus.

16. The intravascular treatment catheter system of claim 15 wherein the first catheter is an over-the-wire (OTW) catheter.

17. The intravascular treatment catheter system of claim 15 wherein the second catheter is a rapid exchange (RX) catheter.

18. The intravascular treatment catheter system of claim 15 wherein the first catheter is an over-the-wire (OTW) catheter and the second catheter is a rapid exchange (RX) catheter that extending through a distal portion of the elongated body substantially parallel to the OTW catheter.

19. The intravascular treatment catheter system of claim 18 wherein the RX catheter comprises a bent portion at a distal end to assist in pointing a distal end of the elongated body as the elongated body moves along the OTW catheter.

* * * * *